United States Patent
Palmisano et al.

(10) Patent No.: US 9,872,751 B2
(45) Date of Patent: Jan. 23, 2018

(54) IMPLANTABLE MEDICAL DEVICE AND METHODS OF DELIVERING THE IMPLANTABLE MEDICAL DEVICE

(71) Applicant: Boston Scientific Scimed, Inc., Maple Grove, MN (US)

(72) Inventors: Brent Palmisano, Fiskdale, MA (US); Sanda Nagale, Lowell, MA (US); Jamie Li, Lexington, MA (US); Mark W. Boden, Harrisville, RI (US); Timothy P. Harrah, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 407 days.

(21) Appl. No.: 14/199,605

(22) Filed: Mar. 6, 2014

(65) Prior Publication Data

US 2014/0257027 A1    Sep. 11, 2014

Related U.S. Application Data

(60) Provisional application No. 61/776,408, filed on Mar. 11, 2013.

(51) Int. Cl.
*A61F 2/00* (2006.01)
*A61B 17/06* (2006.01)

(52) U.S. Cl.
CPC .......... *A61F 2/0063* (2013.01); *A61F 2/0045* (2013.01); *A61B 2017/06052* (2013.01); *A61B 2017/06176* (2013.01); *A61F 2002/0072* (2013.01); *A61F 2220/0016* (2013.01); *A61F 2230/006* (2013.01)

(58) Field of Classification Search
CPC ...... A61B 2017/00805; A61B 17/0401; A61B 2017/06176; A61B 17/0482; A61B 17/06; A61B 17/06066; A61F 2/0045; A61F 2/0061; A61F 2002/0072
See application file for complete search history.

(56) References Cited

U.S. PATENT DOCUMENTS

| | | |
|---|---|---|
| 2002/0189622 A1 | 12/2002 | Cauthen, III |
| 2005/0004576 A1 | 1/2005 | Benderev |
| 2005/0267531 A1 | 12/2005 | Ruff |
| 2009/0076543 A1* | 3/2009 | Maiorino ......... A61B 17/06166 606/228 |

(Continued)

FOREIGN PATENT DOCUMENTS

| WO | 2014164333 A2 | 10/2014 |
|---|---|---|
| WO | 2014164333 A3 | 12/2014 |

OTHER PUBLICATIONS

International Preliminary Report on Patentability for PCT Application No. PCT/US14/21957, dated Sep. 24, 2015, 10 Pages.

(Continued)

*Primary Examiner* — Christine H Matthews
(74) *Attorney, Agent, or Firm* — Brake Hughes Bellermann LLP

(57) ABSTRACT

In one general aspect, an apparatus can include a mesh having an edge, a loop coupled to the edge of the mesh, and a suture coupled to at least one of the loop or the edge of the mesh, the suture having a barb. The loop can have an inner diameter smaller than a combined width of the suture and at least a portion of an outer portion of the barb.

17 Claims, 18 Drawing Sheets

(56) References Cited

U.S. PATENT DOCUMENTS

| | | | |
|---|---|---|---|
| 2009/0171143 A1* | 7/2009 | Chu | A61B 17/0401 600/37 |
| 2009/0221868 A1* | 9/2009 | Evans | A61F 2/0045 600/37 |
| 2009/0228021 A1 | 9/2009 | Leung | |
| 2009/0248071 A1 | 10/2009 | Saint | |
| 2010/0121460 A1* | 5/2010 | D'Afiero | A61B 17/06 623/23.64 |

OTHER PUBLICATIONS

International Search Report and Written Opinion for PCT Application No. PCT/US2014/021957, dated Oct. 16, 2014, 15 Pages.
Invitation to Pay Add'l Fees and Partial Search Report for PCT Application No. PCT/US2014/021957, dated Jul. 29, 2014, 6 Pages.

* cited by examiner

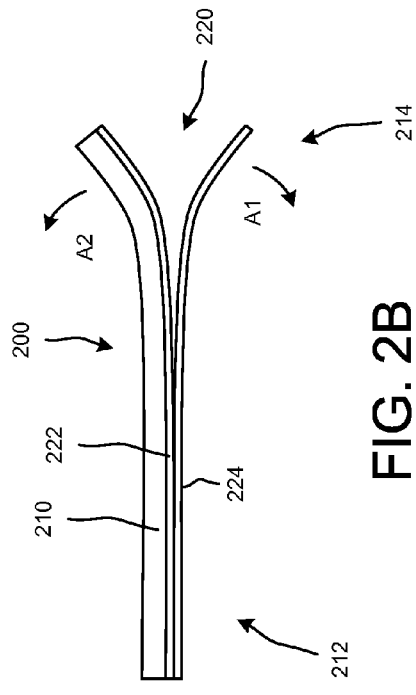
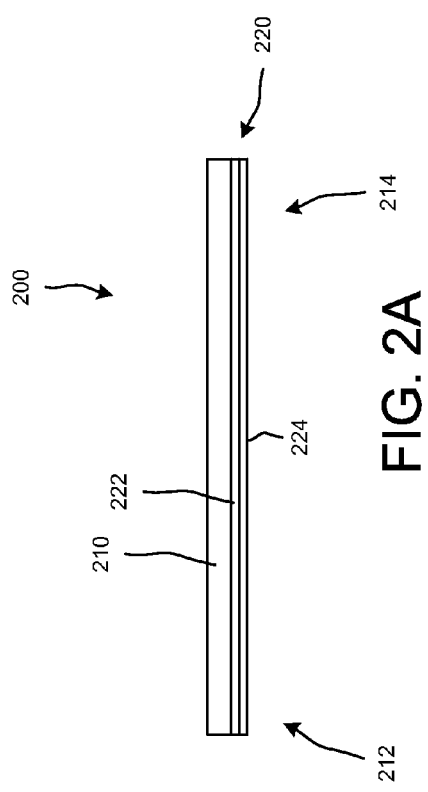
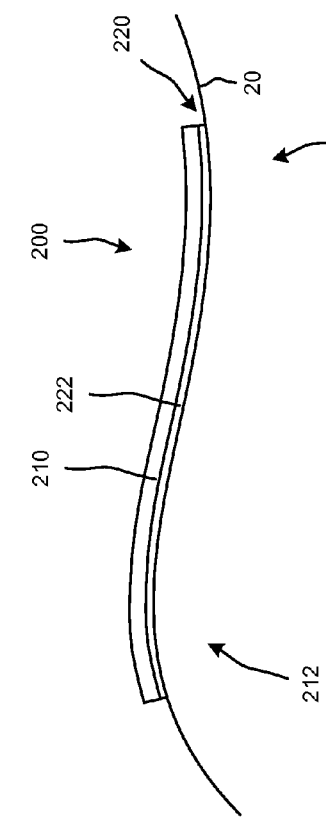
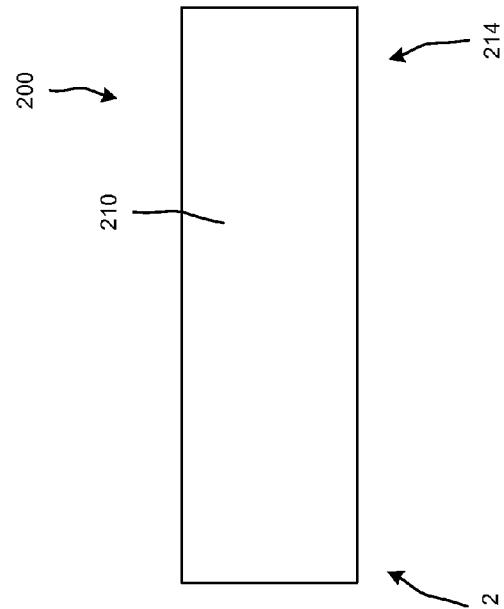
FIG. 2A
FIG. 2B
FIG. 2C
FIG. 2D

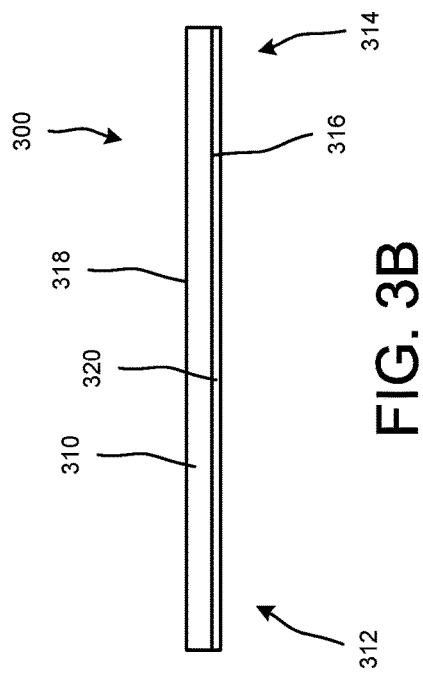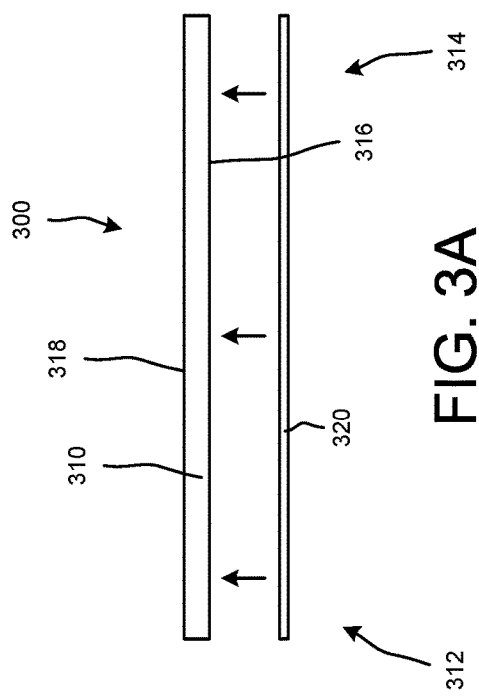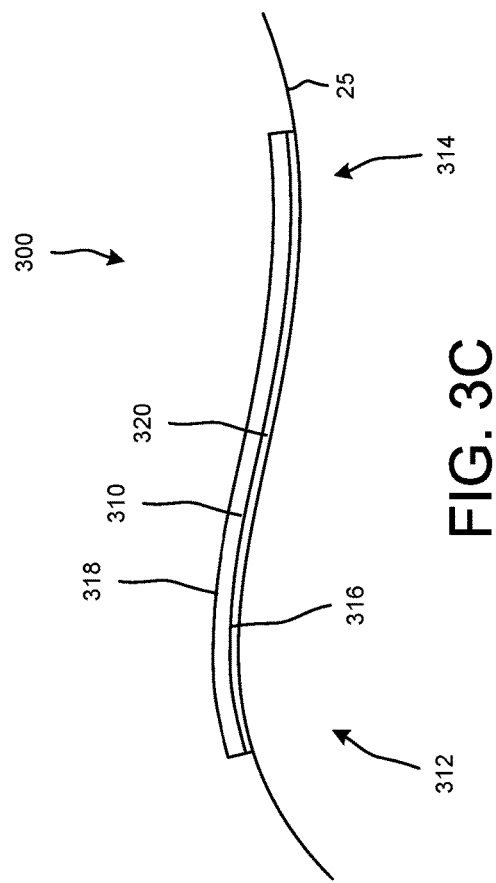

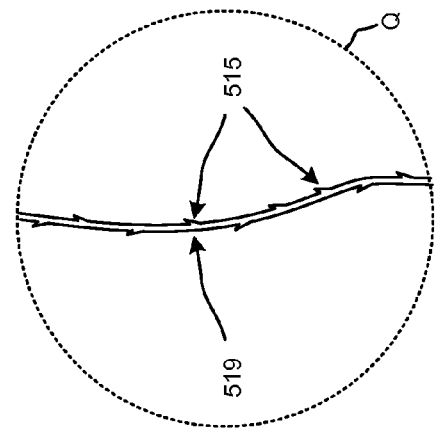
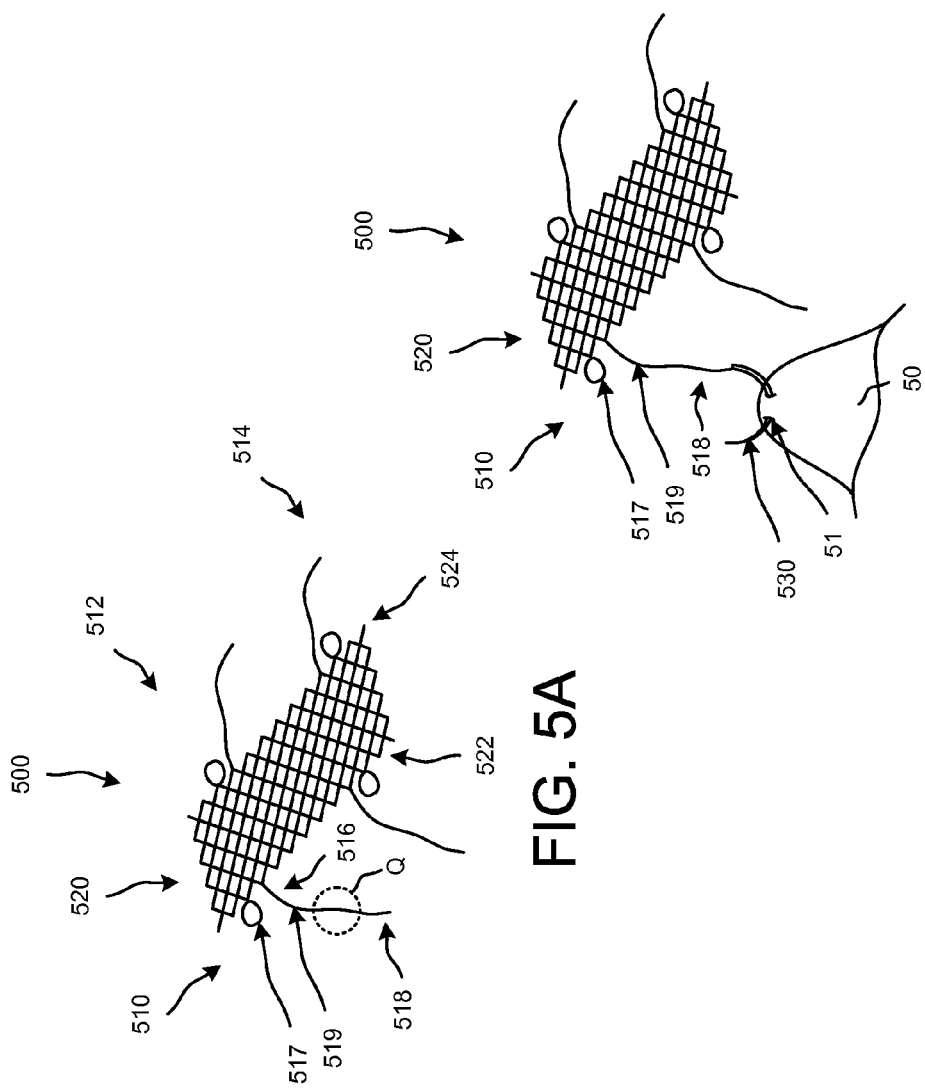
FIG. 5B
FIG. 5C
FIG. 5A

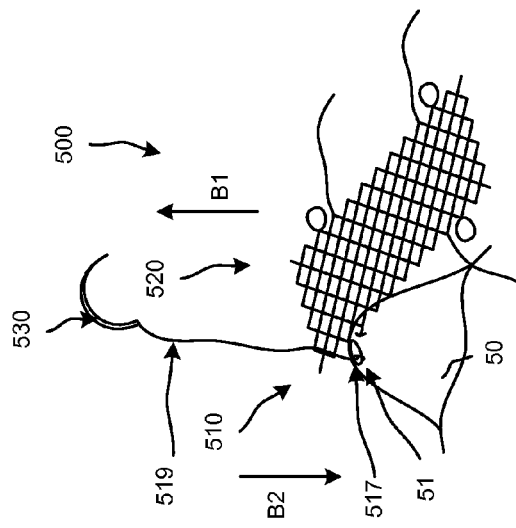
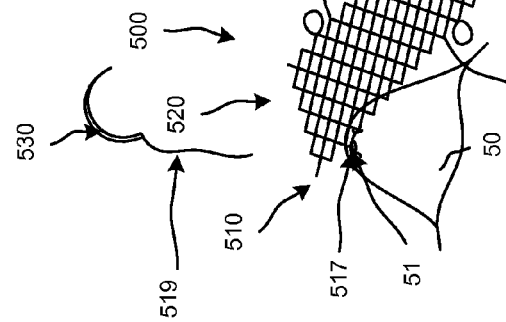
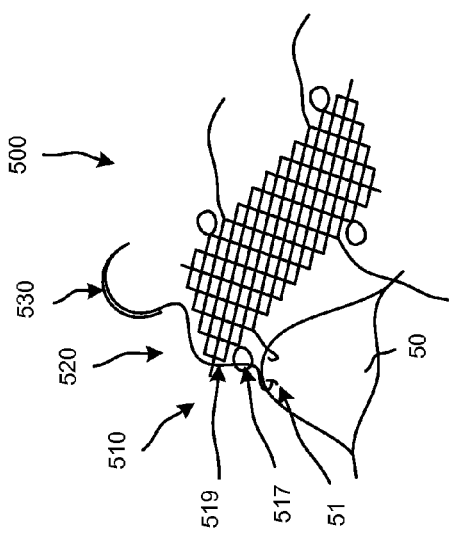

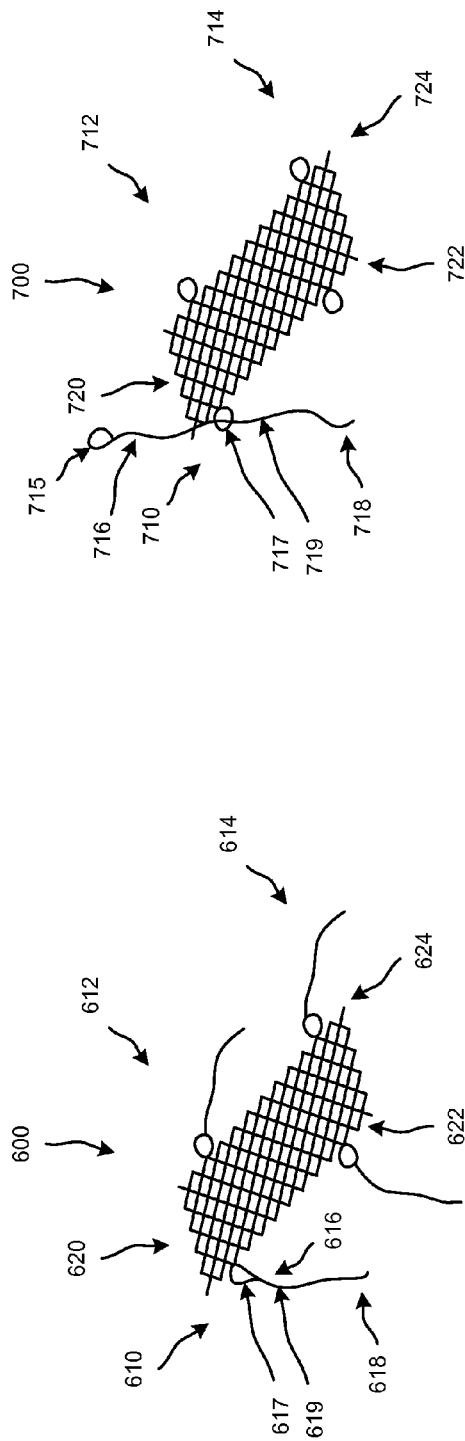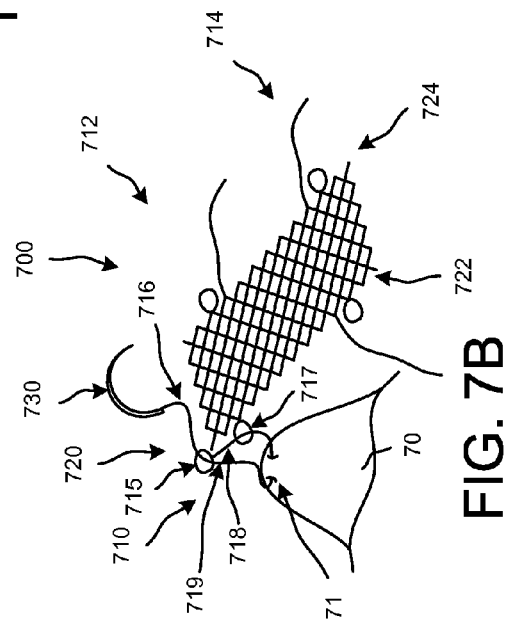

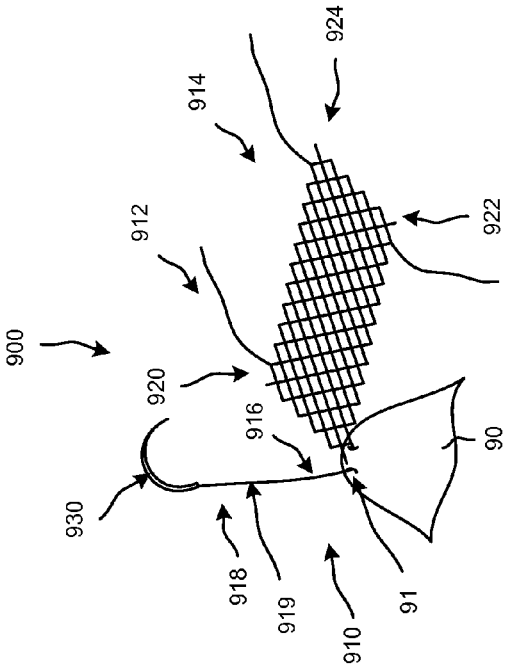
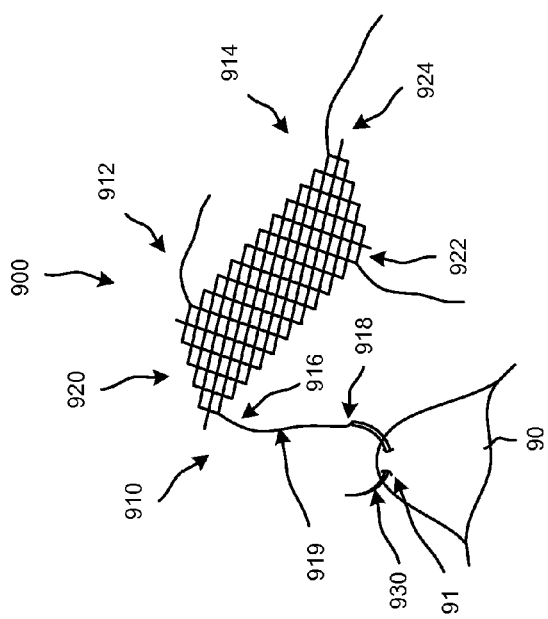

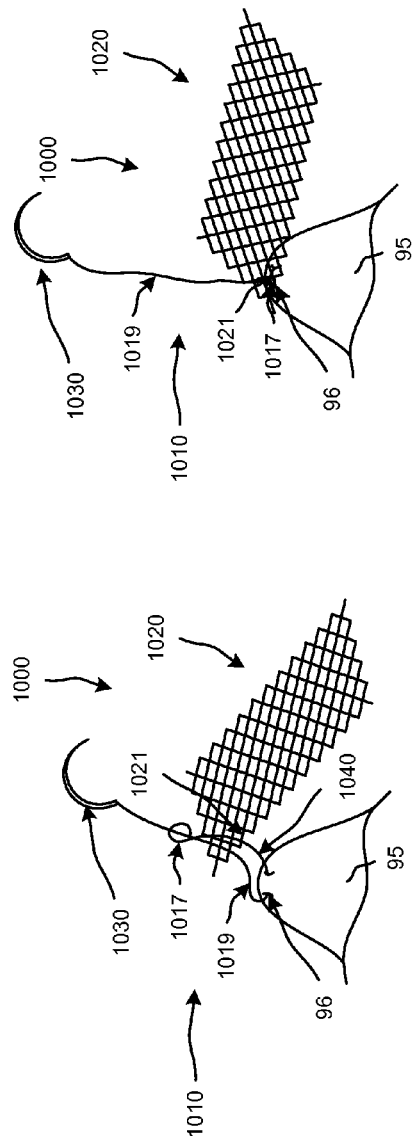
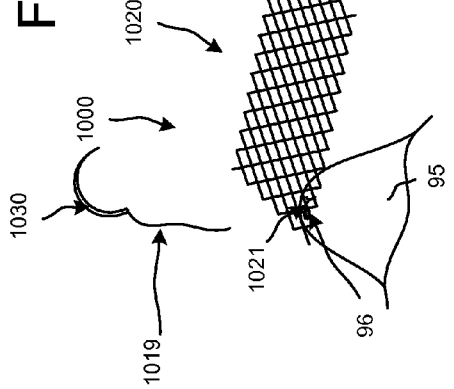
FIG. 10C
FIG. 10D
FIG. 10E

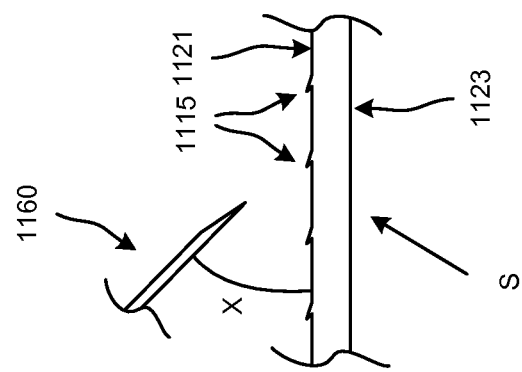
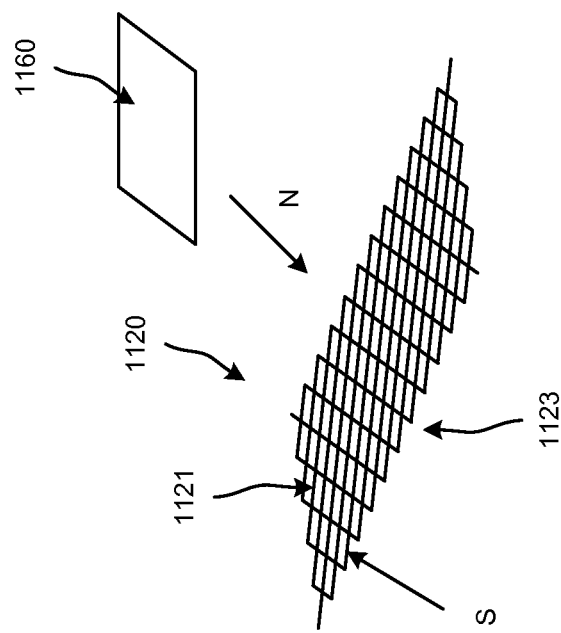
FIG. 11B
FIG. 11A

IMPLANTABLE MEDICAL DEVICE AND METHODS OF DELIVERING THE IMPLANTABLE MEDICAL DEVICE

CROSS REFERENCE TO RELATED APPLICATION

This application is a Nonprovisional of, and claims priority to, U.S. Patent Application No. 61/776,408, filed on Mar. 11, 2013, entitled "IMPLANTABLE MEDICAL DEVICE AND METHODS OF DELIVERING THE IMPLANTABLE MEDICAL DEVICE", which is incorporated by reference herein in its entirety.

TECHNICAL FIELD

The embodiments herein generally relate to medical devices and procedures, particularly devices configured to be delivered and placed into a patient's body.

BACKGROUND

Tissue repair matrices can be used to augment the mechanical properties of tissues, with both immediate and long-term effects. One such application is the use of a polypropylene mesh for the reinforcement and repair of load bearing structures in the female pelvic floor to maintain a desirable anatomical position of one or more organs. In order to effect a repair, a matrix (or mesh) is typically attached on or near a structure of interest. Attachment, which can be referred to as fixation, may involve the use of additional mechanical devices or tools. In some instances, attachment using additional mechanical devices or tools can preserve the relative position of the implant to the structures of interest so that the tissue infiltration, which can provide repair durability, can occur.

Attachment involving known mechanical devices and tools can be time-consuming and complex. In both transvaginal and laparascopic approaches, the mesh can be moved into position and held in place by a physician during the permanent attachment process in accordance with clinical requirements. Using known mechanical devices and tools, mesh manipulation and attachment can be tedious, time-consuming, and technically challenging. Thus, a need exists for systems, methods, and apparatus to address the shortfalls of present technology and to provide other new and innovative features.

SUMMARY

In one general aspect, an apparatus can include a mesh having an edge, a loop coupled to the edge of the mesh, and a suture coupled to at least one of the loop or the edge of the mesh, the suture having a barb. The loop can have an inner diameter smaller than a combined width of the suture and at least a portion of an outer portion of the barb.

BRIEF DESCRIPTION OF THE FIGURES

FIGS. 2A through 2C are schematic block diagrams of side views of a medical device configured to be implanted within a body of a patient. FIG. 2D is a diagram that illustrates a top view of a schematic diagram of the medical device.

FIGS. 3A through 3C are additional schematic block diagrams of side views of a medical device configured to be implanted within a body of a patient.

FIGS. 5A through 5H illustrate a medical device including a loop and a suture.

FIG. 6 illustrates another medical device including a loop and a suture.

FIGS. 7A and 7B illustrate another medical device associated with multiple loops and a suture.

FIGS. 9A and 9B illustrate another medical device including a suture coupled to an edge of a mesh.

FIG. 10A through 10E illustrate another medical device.

FIGS. 11A and 11B illustrate a mesh having a barb.

DETAILED DESCRIPTION

In general, the embodiments disclosed herein are directed to systems, methods, and devices for treating a tissue of a patient with a tissue repair matrix such as mesh. Tissue repair matrices can be used to augment the mechanical properties of diseased structures, with both immediate and long-term effects. Some embodiments can be directed to systems, methods, and devices for treating a tissue of a patient with vaginal prolapse. The embodiments can also be employed for other treatment purposes such as pelvic organ prolapse. As described below in various illustrative embodiments, the embodiments provide systems, methods, and devices employing an improved medical device configured to be implanted within a patient's body to treat a tissue of the patient.

The term patient may be used hereafter for a person who benefits from the medical device or the methods disclosed in the presented embodiments. For example, the patient may be a person whose body receives the medical device disclosed by the present embodiments in a surgical treatment. For example, in some embodiments, the patient may be a human female, a human male, or any other mammal.

The medical devices described herein can be configured to treat conditions such as genital prolapse or pelvic organ prolapse. Genital prolapse or pelvic organ prolapse may include the protrusion of the pelvic organs into or out of the vaginal canal. Pelvic floor prolapse affects many women in the U.S. and almost all of them undergo at least one reconstructive pelvic surgery in their lifetime. Many of the cases may be the result of damage to the vaginal and pelvic support tissue by stretching or tearing of the connective tissue within the pelvic space due to childbirth, age, obesity, post-menopausal conditions or chronically elevated intra-abdominal pressure. The results are the distention of organs such as the bladder and rectum, into the vagina, as well as various stages of vaginal avulsion.

Surgical therapy/technique is usually performed for the treatment of pelvic organ prolapse. These techniques for prolapse treatment include plication of the torn connective tissues and re-suspension of the vagina/uterus. Some traditional suspension techniques include utero-sacral suspension and sacrospinus ligament suspension. Some procedures for vaginal suspension include sacrocolpopexy, where the vagina/uterus is suspended to the sacral promontory with an implanted graft material. Some of the grafts have demonstrated improved long-term success of the repair.

Figure 1:
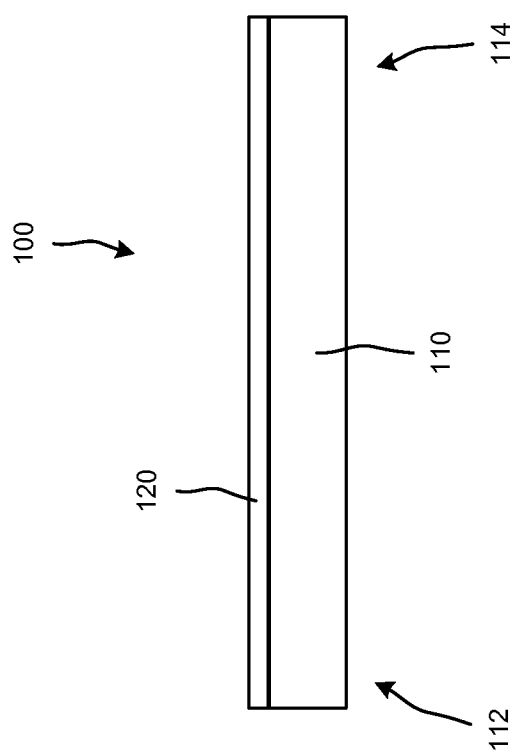
FIG. 1 is a schematic block diagram of a side view of a medical device configured to be implanted within a body of a patient.

FIG. 1 is a schematic block diagram of a side view of a medical device 100 configured to be implanted within a body of a patient. In some embodiments, the medical device 100 is a bodily implant configured to support bodily tissues by augmenting the mechanical properties of, for example, a diseased tissue or structure. In some embodiments, the medical device 100 can be used for hernia repair, to support bodily tissues or organs, plastic and/or reconstructive surgeries, etc. In some embodiments, the medical device 100 can be used for the treatment of pelvic floor prolapse. For example, the medical device 100 can be used, during a medical procedure, to treat various female pelvic dysfunctions, including procedures to treat urinary incontinence, and correcting various prolapse conditions such as uterine prolapse, cystoceles, rectoceles, and vaginal vault prolapse. As another example, in some embodiments, the medical device 100 can be attached to the vagina or another anatomical structure during sacrocolpopexy.

As shown in FIG. 1, the medical device 100 includes an implant and a fixation mechanism and a fixation mechanism 120. In some embodiments, the implant is a mesh 110 (also can be referred to as a mesh member). The medical device 100 has a proximal end portion 112 and a distal end portion 114. In some embodiments, the mesh 110 can be made of, or can include, any combination of a synthetic material(s) or a biologic material(s). In some embodiments, the fixation mechanism 120 of the medical device 100 can include a variety of mechanisms, including, for example, a suture, a staple, a barb, a dart, a mechanical interference device, an adhesive (e.g., a bonding agent), and/or so forth. In some, embodiments, the, fixation mechanism 120 can include. for example, a coating or a layer of a material configured to provide temporary adhesion of the medical device 100 to a tissue. In some embodiments, the fixation mechanism 120 can include one or more mechanical modifications to the mesh 110 that can be configured to enable mechanical fixation of the mesh 110 to a tissue (e.g., mechanical entrapment in a surface of the tissue). In some embodiments, adhesives can include, for example, Fibrin-based tissue adhesives, cyanoacrylates, L-3,4 dihydroxyphenylalnine (DOPA) based adhesives, polysaccharides, peptides, silicone spray on adhesives, and/or so forth.

As mentioned above, the medical device 100 (e.g., the mesh 110 of the medical device 100) can be tissue repair matrix used to augment mechanical properties of tissues (e.g., diseased structures) for short periods of time or for long-term therapies. For example, in some embodiments, the mesh 110 of the medical device 100 can include a polypropylene mesh that can be configured to reinforce or repair a target tissue (e.g., a load-bearing tissue or structure) in a female pelvic floor to maintain a desirable anatomical position and/or function of, for example, a bladder, a uterus, and/or a vagina, The fixation mechanism 120 can be used to temporarily, or permanently, fix the position of the mesh 110 of the medical device 100 in a desirable position with respect to a target tissue. To implement the repair, the medical device 100 can be attached on, or near to, one or more tissues within the female pelvic floor using the fixation mechanism 120, After the medical device 100 has been inserted into the body of the patient, tissue infiltration into the mesh 110 of the medical device 100 to provide repair durability can occur.

In some embodiments, the fixation mechanism 120 can be used as a temporary attachment mechanism. In some embodiments, the fixation mechanism 120 can be a repositionable attachment mechanism. The temporary time period can be, for example, a few minutes, a few hours, a few days, etc. In some embodiments, another mechanism can be used as a long-term or permanent attachment mechanism after the fixation mechanism 120 has been applied and used as a temporary attachment mechanism. The long-term time period can be, for example, more than a few days, a few weeks, a few years, etc. In some embodiments, the permanent attachment mechanisms can include, for example, a suture, an adhesive, a bonding agent, a mechanical fastener (e.g., a clip (e.g., a medical grade plastic clip, a medical grade metal clip), a pin, a clamp, a rivet, an anchor), and/or so forth.

In some embodiments, the fixation mechanism 120 of the medical device 100 can include, or can be associated with, both temporary attachment mechanisms and long-term attachment mechanisms. In some embodiments, a temporary attachment mechanism can be used to temporarily position the medical device 100 with respect to a tissue within a body of the patient for a relatively short period of time. The temporary attachment mechanism can be used to position the medical device 100 until a physician can implement a long-term or permanent attachment mechanism associated with medical device 100. After the temporary attachment mechanism has been used to position the medical device 100, the long-term or permanent attachment mechanism can be used to attach or fix the medical device 100 to the tissue. Accordingly, the temporary attachment mechanism can be used to temporarily attach the medical device 100 until the medical device 100 can be permanently attached using the long-term attachment mechanism. In such embodiments, the temporary attachment mechanism can be configured to be a mechanism (e.g., a relatively simple mechanism) that can be applied, relatively quickly, by the physician during a medical procedure involving the medical device 100 until a long-term or permanent attachment mechanism (which can be more complicated than the temporary attachment mechanism) can be applied.

In some embodiments, the fixation mechanism 120 can remain in a body of a patient after a long-term or permanent attachment mechanism has been applied. In some embodiments, the fixation mechanism 120 can be removed (e.g., disassembled, detached) after a long-term or permanent attachment mechanism has been applied. In some embodiments, the fixation mechanism 120 can also be configured to function as a long-term or permanent attachment mechanism.

In some embodiments, one or more devices (e.g., manipulators) can be used in conjunction with the medical device 100 for coupling (e.g., attachment) of the medical device 100 to a tissue of a patient via the fixation mechanism 120. In some embodiments, one or more devices can be used to hold the medical device 100 against a tissue while implementing the fixation mechanism 120. For example, a device used to facilitate coupling of the medical device 100 to a tissue the patient can include, for example, a balloon, a hemostat, a scalpel, a vaginal manipulator, and/or so forth.

As mentioned above, the mesh 110 can be made of, or can include, a biologic material. The biologic material can be, or can include, for example, an Allograft and/or a Xenograft. In some embodiments, the biologic material can include cadaveric tissue, bovine dermis, porcine dermis, porcine intestinal sub mucosa, bovine pericardium, a cellulose based product, cadaveric dermis, and/or so forth. In some embodiments, the Allograft materials can include Tutoplast®, Repliform®, DuraDerm®, Urogen®, and/or so forth. In some embodiments, the Xenograft materials can include Xenform® (e.g., Xenform Matrix), Stratisis®, Dermatrix® and/or so forth. In some embodiments, the mesh 110 can be made, at least in part, of a biologic material because the biologic material can be relatively robust against tissue erosion. Unlike some materials, the biologic material may not grow into a tissue in an undesirable fashion (e.g., may not grow through a vaginal wall to which the elongate member is attached).

As mentioned above, the mesh 110 can be made of, or can include, a synthetic material. In some embodiments, the synthetic material can be, or can include, for example, as a polymeric mesh body, a polymeric planar body without mesh cells and structures, and/or so forth. In some embodiments, the synthetic material can include polypropylene, polyester, polyethylene, nylon, polyvinyl chloride (PVC), polystyrene, poly (styrene-isobutylene-styrene (SIBS), and/or so forth. In some embodiments, a mesh body of the synthetic material can be made of a non-woven polymeric material. In some embodiments, the synthetic material can include a Polyform® Synthetic Mesh developed by the Boston Scientific Corporation. The Polyform® Synthetic Mesh can be made from uncoated monofilament macroporous polypropylene. In some embodiments, the mesh can be formed of or include a woven structure, a non-woven structure, a knitted structure, or a braided structure. In some embodiments, the mesh is tied, twisted, or layered. In some embodiments, the mesh is formed of single or multifilaments. In some embodiments, the mesh is formed of or includes a sheet or a plurality of sheets and may or may not include pores or openings. In some embodiments, the mesh 110 can have a specified weight. In some embodiments, the mesh weight can be approximately between 15 g/cm² to 35 g/cm² (e.g., 20 g/cm², 25 g/cm², 30 g/cm²). In some embodiments, the mesh 110 can be made, at least in part, of a synthetic material because the synthetic material can have a relatively high strength that can support a bodily portion (e.g., a vaginal apex from attachment at a sacrum) without deforming (e.g., sagging, stretching) over time in an undesirable fashion compared with other materials.

Although not shown in FIG. 1, in some embodiments, the fixation mechanism 120 of the medical device 100 can have a surface area greater than, equal to, or less than, a surface area of the mesh 110 of the medical device 100. For example, in some embodiments, the fixation mechanism 120 can have a distal end that extends beyond or is shorter than a distal end of the mesh 110. Similarly, in some embodiments, the fixation mechanism 120 can have a proximal end that extends beyond or is shorter than a proximal end of the mesh 110. As another example, in some embodiments, the fixation mechanism 120 can have a side (not shown) that extends beyond or is shorter than a side of the mesh 110.

Although not shown in FIG. 1, in some embodiments, the fixation mechanism 120 can include multiple and/or separate portions. Similarly, the mesh 110 can include multiple and or separate portions. The multiple and/or separate portions can have differing surface areas. For example, a first portion of the fixation mechanism 120 can have a different surface area and/or thickness than a second portion of the fixation mechanism 120. As shown in FIG. 1, the fixation mechanism 120 is included on one side of the mesh 110 of the medical device 100. In some embodiments, the medical device 100 can include an additional fixation mechanism (not shown) on another side (e.g., a proximal end portion 112, a distal end portion 114, a bottom portion) of the mesh 110.

FIGS. 2A through 2C are schematic block diagrams of side views of a medical device 200 configured to be implanted within a body of a patient. The medical device 200 shown in FIGS. 2A through 2C can be configured to support bodily tissues by, for example, augmenting the mechanical properties of a diseased tissue or structure.

As shown in FIGS. 2A through 2C, the medical device 200 includes a mesh 210 (also can be referred to as a mesh member) and a fixation mechanism 220. The medical device 200 has a proximal end portion 212 and a distal end portion 214. In some embodiments, the mesh 210 can be made of, or can include, any combination of a synthetic material or a biologic material. In this embodiment, the fixation mechanism 220 includes an adhesive 222 (e.g., an adhesive layer) with a backing material 224 configured to cover the adhesive 222 (or a portion thereof). The backing material 224 can be configured to protect the adhesive 222 from becoming soiled in a manner that will decrease the adhesive capability of the adhesive 222.

As shown in FIG. 2B, the backing material 224 can be removed (e.g., peeled away) from the adhesive 222 prior to use of the medical device 200. In this embodiment, the backing material 224 can be peeled away by moving the backing material 224 starting at the distal end portion 214 of the medical device 200 along direction A1 and moving the remaining portions (e.g., the mesh 210 and adhesive 222) along direction A2.

As shown in FIG. 2C, after the backing material 224 has been removed, the adhesive 222 of the mesh 210 can be applied (e.g., adhered) to a tissue 20 of a patient. In some embodiments, a physician may start to apply the adhesive 222 of the mesh 210 to the tissue 20 of the patient before the backing material 224 has been entirely removed. In some embodiments, the adhesive 222 can be a coating or a layer of the material configured to provide temporary adhesion. In some embodiments, the medical device 200 can be temporarily adhered to the tissue 20 until a more permanent fixation mechanism is applied. In some embodiments, the adhesion of the adhesive 222 to the tissue 20 can be based on a physical mechanism, an ionic mechanism, a van der waals mechanism, and/or can based on reaction between the tissue 20 and the adhesive (e.g., a polymerization reaction with a surface of the tissue 20).

FIG. 2D is a diagram that illustrates a top view of a schematic diagram of the medical device 200 including the mesh 210. In this embodiment, the fixation mechanism 220 cannot be seen because the fixation mechanism 222 is below the mesh 210 of the medical device 200. As shown in FIG. 2D, the medical device 200 has a rectangular shape or profile. In some embodiments, the medical device 200 can have a shape different than a rectangular shape or profile such as a circular shape or profile, an oval shape or profile. In some embodiments, the medical device 200 can have portions that are curved and/or portions that are straight or flat.

Although not shown in FIGS. 2A through 2D, in some embodiments, the fixation mechanism 220 of the medical device 200 can have a surface area greater than, equal to, or less than, a surface area of the mesh 210 of the medical device 200. Although not shown in FIGS. 2A through 2D, the fixation mechanism 220 and/or the mesh 210 can include multiple and or separate portions.

In some embodiments, the medical device 200 can be cut during a procedure in accordance with an anatomy of the patient. In other words, the medical device 200 can be cut so that the medical device 200 can be adhered to a tissue of the patient and a desirable fashion. In some embodiments, a tool used to cut the medical device 200 can be included in a kit with the medical device 200.

FIGS. 3A through 3C are additional schematic block diagrams of side views of a medical device 300 configured to be implanted within a body of a patient. The medical device 300 shown in FIGS. 3A through 3C can be configured to support bodily tissues by, for example, augmenting the mechanical properties of a diseased tissue or structure. The medical device 300 has a proximal end portion 312 and a distal end portion 314. In some embodiments, the mesh 310 can be made of, or can include, any combination of a synthetic material or a biologic material.

As shown in FIG. 3A, a fixation mechanism 320 can be coupled to a side 316 of a mesh 310 in the configuration shown in FIG. 3B so that the medical device 300 can be applied to a tissue 25 of the patient as shown in FIG. 3C. In some embodiments, the fixation mechanism 320 can be coupled to the mesh 310 during a perioperative period or before a surgical procedure has started. In some embodiments, fixation mechanism 320 can be coupled to the mesh 310 during, for example, a laparoscopic procedure and/or a transvaginal procedure.

In some embodiments, the fixation mechanism 320 can be applied to the mesh 310 using an applicator instrument (not shown). For example, the fixation mechanism 320 can be a liquid form adhesive that is sprayed on to the mesh 310 or rolled on to the mesh 310 using a roller type mechanism or a brush. As another example, the fixation mechanism 320 can be a double-sided tape (e.g., a biologically compatible doubled-sided tape, a biodegradable tape). In some embodiments, the fixation mechanism 320 can be applied in limited locations (e.g., sparsely, applied as dots) sufficient for temporary fixation. Although not shown, in some embodiments, the fixation mechanism 320 (e.g., adhesive) can be a two-part composition, in which one part is applied to the mesh 310, and the other part is applied to the tissue 25. In this case, the fixation mechanism 320 can cure (e.g., mechanically and/or chemically bond or change) when the two parts are combined (e.g., brought together, contacted). In another embodiment, the fixation mechanism 320 (e.g., adhesive) can be applied only to the tissue 25, or to both the tissue 25 and the mesh 310. In some embodiments, the adhesive may be activated by any such triggers such as body fluid, body heat, pH, body chemistry, physical stretching or crushing, an activator such as a solvent or reactive chemical, light, etc. In some embodiments any of such triggers may affect a protective layer or coating over the adhesive and expose it to tissues for use. In some embodiments, such a protective coating or layer may be biodegradable to allow exposure of the adhesive to tissues some time after implantation. Although not shown in FIGS. 3A through 3C, in some embodiments, after the medical device 300 has been applied to the tissue 25 of the patient, a permanent or resorbable adhesion barrier can be applied on a side 318 of the mesh 310 opposite the side 316 to prevent unwanted tissue contact from other tissues around the tissue 25. In some embodiments, the mesh 310, the fixation mechanism 320, and/or an applicator instrument can be included in a kit that can be used by a physician during a medical procedure.

Although not shown in FIGS. 3A through 3C, in some embodiments, the mesh 310 can be applied to the tissue 25 of the patient and the fixation mechanism 320 (such as an adhesive (e.g., a liquid adhesive)) can be applied to the mesh 310 while in contact with the tissue 25. For example, the fixation mechanism 320 can be applied as a coating on top side (or top surface) of the mesh 310 while the mesh is in contact with the tissue 25. In such embodiments, at least a portion of the fixation mechanism 320 can come into contact with the tissue 25 through at least a portion of one or more openings in the mesh 310. Accordingly, the fixation mechanism 320 can hold the mesh 310 in place on the tissue 25 through contact with both the mesh 310 and the tissue 25.

In some embodiments, the medical device 300 can have one of a variety of shapes or profiles (e.g., a rectangular shape or profile, a circular shape or profile, an oval shape or profile). In some embodiments, the medical device 300 can have portions that are curved and/or portions that are straight. Although not shown in FIGS. 3A through 3C, in some embodiments, the fixation mechanism 320 of the medical device 300 can have a surface area greater than, equal to, or less than, a surface area of the mesh 310 of the medical device 300. Although not shown in FIGS. 3A through 3C, the fixation mechanism 320 and/or the mesh 310 can include multiple and or separate portions.

In some embodiments, the medical device 300 can be cut during a procedure in accordance with an anatomy of the patient. In other words, the medical device 300 can be cut so that the medical device 300 can be adhered to a tissue of the patient and a desirable fashion. In some embodiments, the mesh 310 can be cut before the fixation mechanism 320 is applied, or after the fixation mechanism 320 has been applied. In some embodiments, a tool used to cut the medical device 300 can be included in a kit with the medical device 300.

Figure 4:
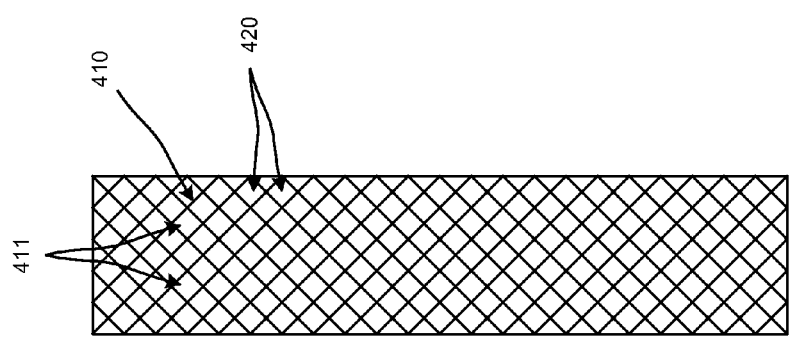
FIG. 4 is a diagram that illustrates a mesh.

FIG. 4 is a diagram that illustrates a mesh 410, according to an embodiment. As shown in FIG. 4, at least some portions of a fixation mechanism 420 such as an adhesive or another material can be exposed through openings 411 of the mesh 410. In some embodiments, at least some portions of a fixation mechanism 420 such as an adhesive or another material can be embedded within the openings 411 of the mesh 410. The mesh 410 shown in FIG. 4 can be an example of a mesh that is used in any of the embodiments described herein.

Figure 5H:
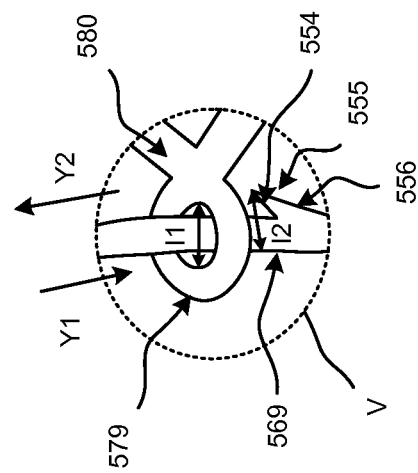

FIGS. 5A through 5H illustrate a medical device 500 including a loop 517 and a suture 519, according to an embodiment. As shown in FIG. 5A, the medical device 500 includes a mesh 520 and a fixation mechanism 510, which includes the loop 517 and the suture 519. In this embodiment, the mesh 520 includes multiple fixation mechanisms similar to the fixation mechanism 510. In some embodiments, the loop 517, the suture 519, and the mesh 520 can be made of the same material or of different materials. The elements included in the medical device 500 may have different relative dimensions than shown in FIGS. 5A through 5F. For example, the loop 517 can be smaller or larger and/or the length of the suture 519 may be shorter or longer than shown in FIGS. 5A through 5F. An example of a relatively small loop that can be included in the embodiment shown FIGS. 5A through 5F is described, for example, in connection with FIGS. 5G and 5H.

As shown in FIG. 5A, the loop 517 is coupled to an edge 522 of the mesh 520. Similarly, the suture 519 (e.g., a distal end 516 of the suture 519) is coupled to the edge 522 of the mesh 520. In this embodiment, the loop 517 is coupled to the edge 522 at a first location, and the suture 519 is coupled to the edge 522 at a second location. In some embodiments, rather than being coupled to the edge 522 of the mesh 520, the loop 517 and/or the suture 519 can be coupled to a top side of the mesh 520 (the flat side of the mesh seen in FIG. 5A), a bottom side or bottom surface) of the mesh 520 (the flat side of the mesh that is not visible in FIG. 5A), or any edge of the mesh 520. In some embodiments, rather than being coupled to a common edge (i.e., edge 522 of the mesh 520) or side of the mesh 520, the loop 517 and the suture 519 can be coupled to different edges (or sides) of the mesh 520. In some embodiments, an opening formed by the loop 517 can have a circular shape, an oval shape, a square shape, and/or so forth.

In this embodiment, fixation mechanisms (not labeled) similar to fixation mechanism 510 are coupled to an edge 524 of the mesh 520, which is on an opposite side of the mesh 520 relative to the edge 522. In this embodiment, two fixation mechanisms are coupled to a proximal end portion 512 of the mesh 520 and two fixation mechanisms are coupled to a distal end portion 514 of the mesh 520. Accordingly, in this embodiment, the medical device 500 includes a total of four fixation mechanisms. In some embodiments, the mesh 520 can include more fixation mechanisms (e.g., 6 fixation mechanisms) or less fixation mechanisms than those shown. For example, one or more fixation mechanisms can be coupled to only the proximal end portion 512 of the mesh 520. As another example, fixation mechanisms may be coupled to only the edge 522 of the mesh 520. In such embodiments, one or more fixation mechanisms may not be coupled to the edge 524. In some embodiments, more fixation mechanisms can be associated with the edge 524 of the mesh 520 than the edge 522 of the mesh 520.

FIG. 5B is a diagram that illustrates a zoomed-in depiction of portion Q of the suture 519 shown in FIG. 5A. As shown in FIG. 5B, the suture 519 includes several barbs 515. In some embodiments, the barbs 515 can be larger or smaller, relative to the suture 519, than shown in FIG. 5B. Although not shown in FIG. 5B, in some embodiments, different types of barbs with the different densities along the suture 519 can be included in the suture 519. One or more barbs can be located around the suture 519—similar to the spines of an umbrella. Although not shown in connection with FIGS. 5A through 5H, other portions of the fixation mechanism 510 and/or of the mesh 520 of the medical device 500 can include one or more barbs. Details associated with such embodiments are described in connection with figures below.

In some embodiments, instead of, or in addition to, the suture 519 and the loop 517, at least a portion of (e.g., a proximal end of) the suture 519 proximal to the mesh 520 construct can have an interference mechanism (not shown) such as a spherical-shaped bead (or other shape such as a cone where the narrower side of the cone is proximal to the needle 530) with a diameter 2 to 5 times (e.g., at least 3 times) a cross-sectional diameter of the suture 519. The interference mechanism can be configured to be pulled through the opening 51 (e.g., piercing) in the tissue 50 formed by the needle 530. After the interference mechanism has passed through the opening 51 of the tissue 50, the shape of the interference mechanism can substantially prevent movement of the suture 519 in an opposite direction out of the opening 51 and can thus secure the mesh 520 to (e.g., next to) the tissue 50. The interference mechanism can also be configured with a flexible shape (e.g., shaped like an umbrella) so that the interference mechanism can pass through the tissue piercing 51 (in a shape of closed umbrella) but after the interference mechanism has passed through tissue, the interference mechanism can expand (e.g., similar to an open umbrella) and thus prevents the suture 519 from moving in the opposite direction. The interference mechanism can be configured to expand around at least a portion of or around the entire circumference of the suture 519. Accordingly, the interference mechanism can have a shape that can be modified or can be changed from a contracted shape (or configuration) to an expanded shape (or configuration). The interference mechanism can be configured to be in a first configuration before being moved through the opening 51 of the tissue 50, can be a second configured while moving through the opening 51 of the tissue 50, and can return to the first configuration after moving through the opening 51 of the tissue 50.

FIGS. 5C through 5H that are diagrams that illustrate attachment of the mesh 520 to a tissue 50. As shown in FIG. 5C, a proximal end 518 of the suture 519 can be coupled to a needle 530. In some embodiments, corresponding pairs of needles (e.g., needle 530), sutures (e.g., suture 519), and/or loops (e.g., loop 517) may be color coded. The needle 530 can be used to pierce the tissue 50 to form an opening 51. As shown in FIG. 5D, the needle 530 can be moved through (e.g., completely through) the opening 51 in the tissue 50, which is formed by the needle 530, so that the suture 519, which is attached to the needle 530, can also be moved through the opening 51. Also, as shown in FIG. 5D, the needle 530 can be threaded through the loop 517 (e.g., an opening formed by the loop 517) so that the suture 519 can be threaded through the loop 517. The needle 530 is shown as a curved needle, but in some embodiments, the needle 530 can be a needle with a different shape such as a straight needle.

As shown in FIG. 5E, after the needle 530 is threaded through the loop 517, the needle 530 can be moved along direction B1 (which is away from the tissue 50) so that at least a portion of the mesh 520 can be moved in an opposite direction along direction B2 toward the tissue 50 (using the opening 51 of the tissue 50 as a pulley). In other words, the mesh 520 can be moved toward the tissue 50 in a desirable fashion using the fixation mechanism 510. In some embodiments, the mesh 520 can be moved toward the tissue 50 by tightening the fixation mechanism 510 in the manner described above. In some embodiments, the mesh 520 may not be in contact with (e.g., may be separated from) the tissue 50 after tightening of the fixation mechanism 510 is performed. In some embodiments, at least a portion of the loop 517 can be embedded in the tissue 50 via the opening 51. In such embodiments, the mesh 520 may be in a desirable position with respect to the tissue 50 when the mesh 520 is not in contact with the tissue 50. In some embodiments, after the mesh 520 has been moved to a desirable position with respect to the tissue 50, a knot (e.g., a tether) can be tied (e.g., tied by a physician) using the suture 519 and/or the loop 517.

Because the suture 519 has barbs 515, the suture 519 can be prevented (or substantially prevented) from moving out of the opening 51 in the tissue 50. In other words, the barbs 515 of the suture 519 can be configured so that when the suture 519 has been moved into the tissue 50 in a first direction, the barbs 515 of the suture 519 can prevent (or substantially prevent) the suture 519 from moving in a second direction opposite the first direction. In some embodiments, the suture 519 may not include barbs 515. In such embodiments, the suture 519 can be slidably moved through the opening 51 of the tissue 50 in the first direction or the second direction.

After the mesh 520 has been moved to a desirable position with respect to the tissue 50, at least a portion of the suture 519 (which is coupled to the needle 530) can be removed (e.g., removed by cutting) as shown in FIG. 5F. In other words, excess portions of the suture 519 can be removed after the mesh 520 is moved to a desirable position with respect to the tissue 50. In some embodiments, the mesh 520 (which is coupled to the fixation mechanism 510), the needle 530, and/or a device used to cut the suture 519 can be included in a kit that can be used during a medical procedure.

Figure 5G:
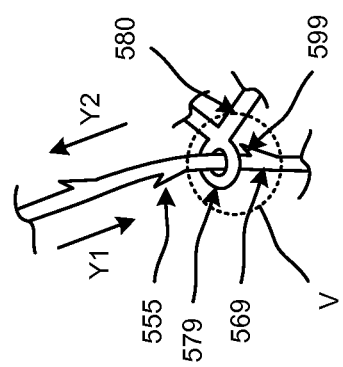

FIG. 5G is a diagram that illustrates a mesh 580 coupled to a loop 579. As shown in FIG. 5G, a suture 569 with barbs 555 can be threaded through the loop 579. The barbs 555 and the suture 569 are configured (e.g., sized) so that the suture 569 can be threaded through the loop 579 along direction Y, but can be configured (e.g., sized) so that the suture 569 can be substantially prevented from moving along direction Y2. Specifically, the suture 569 can be prevented from moving along direction Y2 when a portion (e.g., a tip) of at least one of the barbs 555 becomes engaged with the loop 579. The size (e.g., an inner diameter) of the loop 579 can be configured so that the barbs 555 can move through the loop 579 along direction Y1, but not along direction Y2. FIG. 5H is a diagram that illustrates a zoomed in depiction of portion V of one of the barbs 555 and the loop 579.

As shown in FIG. 5H, the loop 579 has an inner diameter I1 (of an opening defined by the inner diameter I1) that is smaller than a width I2 of the suture 569 and at least a portion of an outer portion 556 of the barb 555. In some embodiments, the width I2 can be referred to as a combined width of the suture 569 and at least a portion of the barb 555. In some embodiments, the loop 579 and/or the barb 555 can be configured from a relatively flexible material so that the barb 555 can be moved through the loop 579 along direction Y1 when the barb 555 comes in contact with (e.g., engages with) the loop 579, but may not be moved in the opposite direction Y2 when the barb 555 comes in contact with (e.g., engages with) the loop 579. For example, as shown in FIG. 5H, the outer portion 556 of the barb 555 has a slope that allows the barb 555 to be moved along direction Y1 through the opening of the loop 579 (when the outer portion 556 is in contact with at least a portion of the loop 579). The barb 555 also has an inner portion 554 that has a slope that prevents the barb 555 from being moved along direction Y2 through the opening of the loop 579 (when the inner portion 554 is in contact with at least a portion of the loop 579). The embodiment shown in FIGS. 5G and 5H can be applied to any of the loop, suture, and barb embodiments described herein.

FIG. 6 illustrates another medical device 600 including a loop 617 and a suture 619, according to an embodiment. As shown in FIG. 6, the medical device 600 includes a mesh 620 and a fixation mechanism 610. In this embodiment, the mesh 620 includes multiple fixation mechanisms similar to the fixation mechanism 610.

As shown in FIG. 6, the loop 617 is coupled to an edge 622 of the mesh 620, and the suture 619 (e.g., a distal end 616 of the suture 619) is coupled to the loop 617. In such embodiments, the loop 617 may not be directly coupled to the mesh 620. In some embodiments, the loop 617 can be coupled to a top side of the mesh 620 (the flat side of the mesh seen in FIG. 6A), a bottom side of the mesh 620 (the flat side of the mesh that is not visible in FIG. 6A), or any edge of the mesh 620. In some embodiments, an opening formed by the loop 617 can have a circular shape, an oval shape, a square shape, and/or so forth. In some embodiments, rather than the suture 619 being coupled to the loop 617, the distal end 616 of the suture 619 can be coupled to the edge 622 of the mesh 620 and the loop 617 can be coupled to the suture 619. In some embodiments, the loop 617, the suture 619, and the mesh 620 can be made of the same material or of different materials.

The elements included in the medical device 600 may have different relative dimensions than shown in FIG. 6. For example, the loop 616 can be smaller or larger and/or the length of the suture 619 may be shorter or longer than shown in FIG. 6. An example of a relatively small loop that can be included in FIG. 6 is shown and described, for example, in connection with FIGS. 5G and 5H.

In this embodiment, fixation mechanisms (not labeled) similar to fixation mechanism 610 are coupled to an edge 624 of the mesh 620, which is on an opposite side of the mesh 620 relative to the edge 622. In this embodiment, the medical device 600 includes a total of four fixation mechanisms. In some embodiments, the mesh 620 can include more fixation mechanisms or less fixation mechanisms than those shown, and fixation mechanisms can be coupled to any portion (e.g., top side, bottom side, edge 622, edge 624) of the mesh 620. Although not shown in FIG. 6, the loop 617, the suture 619, and/or the mesh 620 can include one or more barbs.

The mesh shown in FIG. 6 can be attached to a tissue of a patient in a fashion similar to that shown and described in connection with FIGS. 5C through 5H. A proximal end 618 of the suture 619 can be coupled to a needle (not shown). The needle can be used to pierce a tissue to form an opening through which the suture 619 can be moved. The needle and the suture 619 can be threaded through the loop 617 (e.g., an opening formed by the loop 617). The mesh 620 can be moved to a desirable position with respect to the tissue using the fixation mechanism 610. The mesh 620 can be moved to a desirable position with respect to the tissue 60 using the fixation mechanism 610 (e.g., by tightening the fixation mechanism 610). For example, the needle 630, and suture 619 coupled thereto, can be pulled in an upward direction away from the tissue 60 through the loop 617 to cause the mesh 620 (and loop 617) to be moved toward the tissue 60. In some embodiments, at least a portion of the loop 617 can be embedded in the tissue 60 via the opening 61. In some embodiments, after the mesh 620 has been moved to a desirable position with respect to the tissue, a knot (e.g., a tether) can be tied (e.g., tied by a physician) using the suture 619 and/or the loop 617. Finally, excess portions of the suture 619 can be removed after the mesh 620 is moved to a desirable position with respect to the tissue. In some embodiments, the mesh 620 (which is coupled to the fixation mechanism 610), the needle, and/or a device used to cut the suture 619 can be included in a kit that can be used during a medical procedure. The needle 630 is shown as a curved needle, but in some embodiments, the needle 630 can be a needle with a different shape such as a straight needle.

FIG. 7A illustrates another medical device 700 associated with multiple loops 715, 717 and a suture 719, according to an embodiment. As shown in FIG. 7A, the medical device 700 includes a mesh 720 and a fixation mechanism 710. The multiple loops 715, 717 and the suture 719 can collectively define the fixation mechanism 710 of the medical device 700. In some embodiments, the loops 715, 717, the suture 719, and the mesh 720 can be made of the same material or of different materials. The elements included in the medical device 700 may have different relative dimensions than shown in FIGS. 7A and 7B. For example, the loop 715 and/or the loop 717 can be smaller or larger and/or the length of the suture 719 may be shorter or longer than shown in FIGS. 7A and 7B. An example of a relatively small loop that can be included in FIGS. 7A and 7B is shown and described, for example, in connection with FIGS. 5G and 5H.

As shown in FIG. 7A, the loop 717 is coupled to an edge 722 of the mesh 720, and the loop 715 is coupled to the suture 719 (e.g., a distal end 716 of the suture 719). In some embodiments, the loop 717 can be coupled to a top side of the mesh 720 (the flat side of the mesh seen in FIG. 7A), a bottom side of the mesh 720 (the flat side of the mesh that is not visible in FIG. 7A), or any edge of the mesh 720. In some embodiments, an opening formed by the loop 715 and/or the loop 717 can have a circular shape, an oval shape, a square shape, and/or so forth. In some embodiments, the loop 717 can be referred to as a mesh loop, and the loop 715 can be referred to as a suture loop. In some embodiments, the loop 715 and the suture 719 can collectively be referred to as a suture-loop member. Although not shown in FIG. 7A, each of the additional loops (not labeled) similar to loop 717 can be associated with a suture-loop member (not shown) similar to the suture 719 coupled to the loop 715 (which is also a suture-loop member).

In this embodiment, fixation mechanisms (not labeled) similar to fixation mechanism 710 can be associated with an edge 724 of the mesh 720, which is on an opposite side of the mesh 720 relative to the edge 722. In some embodiments, the mesh 720 can include more fixation mechanisms or less fixation mechanisms than those shown, and fixation mechanisms can be coupled to any portion (e.g., top side, bottom side, edge 722, edge 724) of the mesh 720. Although not shown in FIG. 7A, the loop 715, the loop 717, the suture 719, and/or the mesh 720 can include one or more barbs.

The mesh shown in FIG. 7A can be attached to a tissue of a patient in a fashion similar to that shown and described in connection with FIGS. 5C through 5H. A proximal end 718 of the suture 719 can be coupled to a needle 730. The needle 730 and the suture 719 can be threaded through the loop 717 (e.g., an opening formed by the loop 717). The needle 730 can be used to pierce a tissue 70 to form an opening 71 through which the suture 719 can be moved. After the opening 71 in the tissue 70 has been formed, the needle 730 and the suture 719 can be threaded through the loop 715 (e.g., an opening formed by the loop 715) as shown in FIG. 7B. In some embodiments, the needle 730 and the suture 719 (which is a suture-loop member) can be threaded through the loop 717 after the opening 71 has been formed in the tissue 70 using the needle 730. The mesh 720 can be moved to a desirable position with respect to the tissue 70 using the fixation mechanism 710 (e.g., by tightening the fixation mechanism 710). For example, the needle 730, and suture 719 coupled thereto, can be pulled in an upward direction away from the tissue 70 through the loop 715 to cause the mesh 720 (and loop 717) to be moved toward the tissue 70. In some embodiments, at least a portion of the loop 715 and/or loop 717 can be embedded in the tissue 70 via the opening 71 during a medical procedure. In some embodiments, after the mesh 720 has been moved to a desirable position with respect to the tissue, a knot (e.g., a tether) can be tied (e.g., tied by a physician) using the suture 719 and/or the loop 717. Finally, excess portions of the suture 719 can be removed after the mesh 720 is moved to a desirable position with respect to the tissue 70. In some embodiments, the mesh 720 (which is coupled to the fixation mechanism 710), the loop 715 and the suture 719, the needle 730, and/or a device used to cut the suture 719 can be included in a kit that can be used during a medical procedure. The needle 730 is shown as a curved needle, but in some embodiments, the needle 730 can be a needle with a different shape such as a straight needle.

Figure 8B:
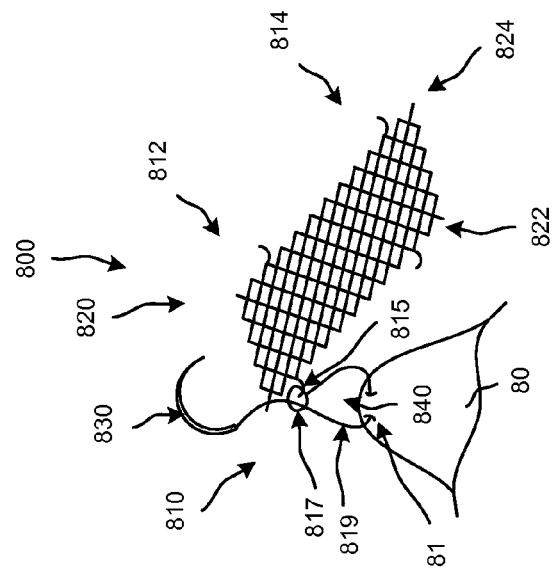
FIGS. 8A and 8B illustrate another medical device including a hook and a suture coupled to a loop.
Figure 8A:
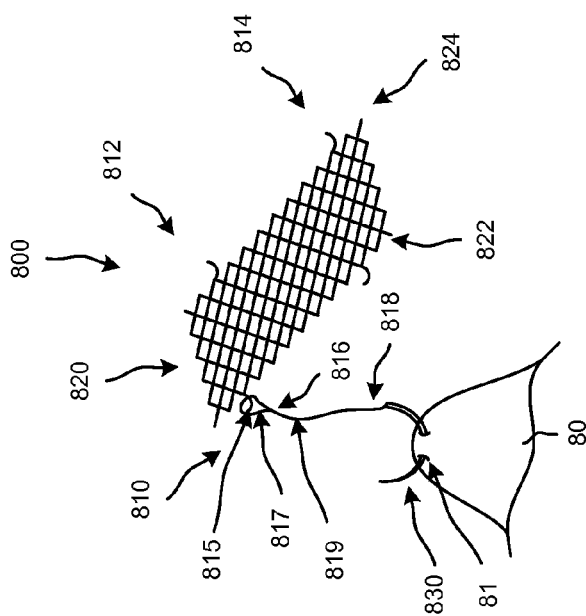

FIG. 8A illustrates another medical device 800 including a hook 815 and a suture 819 coupled to a loop 817, according to an embodiment. As shown in FIG. 8A, the medical device 800 includes a mesh 820 and a fixation mechanism 810. The hook 815, the loop 817, and the suture 819 can collectively define the fixation mechanism 810 of the medical device 800. In some embodiments, the loop 817, the hook 815, the suture 819, and the mesh 820 can be made of the same material or of different materials. In some embodiments, the loop 817, the hook 815, the suture 819, and the mesh 820 can be made of the same material or of different materials. The elements included in the medical device 800 may have different relative dimensions than shown in FIGS. 8A and 8B. For example, the loop 815 and/or the hook 815 can be smaller or larger and/or the length of the suture 819 may be shorter or longer than shown in FIGS. 8A and 8B. An example of a relatively small loop that can be included in FIGS. 8A and 8B is shown and described, for example, in connection with FIGS. 5G and 5H.

As shown in FIG. 8A, the hook 815 is coupled to an edge 822 of the mesh 820, and the loop 817 is coupled to the suture 819 (e.g., a distal end 816 of the suture 819). In some embodiments, the hook 815 can be coupled to a top side of the mesh 820 (the flat side of the mesh seen in FIG. 8A), a bottom side of the mesh 820 (the flat side of the mesh that is not visible in FIG. 8A), or any edge of the mesh 820. In some embodiments, an opening formed by the loop 817 can have a circular shape, an oval shape, a square shape, and/or so forth. In some embodiments, the loop 817 can be referred to as a suture loop. In some embodiments, the loop 817 and the suture 819 can collectively be referred to as a suture-loop member. Although not shown in FIG. 8A, each of the additional hooks (not labeled) similar to hook 815 can be associated with a suture-loop member (not shown) similar to the suture 819 coupled to the loop 817 (which is also a suture-loop member).

In this embodiment, fixation mechanisms (not labeled) similar to fixation mechanism 810 can be associated with an edge 824 of the mesh 820, which is on an opposite side of the mesh 820 relative to the edge 822. In some embodiments, the mesh 820 can include more fixation mechanisms or less fixation mechanisms than those shown, and fixation mechanisms can be coupled to any portion (e.g., top side, bottom side, edge 822, edge 824) of the mesh 820. Although not shown in FIG. 8A, the hook 815, the loop 817, the suture 819, and/or the mesh 820 can include one or more barbs.

The mesh shown in FIG. 8A can be attached to a tissue of a patient in a fashion similar to that shown and described in connection with FIGS. 5C through 5H. A proximal end 818 of the suture 819 can be coupled to a needle 830, and the loop 817 can be coupled to the hook 815. The needle 830 can be used to pierce a tissue 80 to form an opening 81 through which the suture 819 can be moved. The mesh 820 can be moved to a desirable position with respect to the tissue 80 by moving the suture 819 through the opening 81, which will cause movement of the mesh 820 via the hook 815. In some embodiments, at least a portion of the hook 815 and/or the loop 817 can be embedded in the tissue 80 via the opening 81. In some embodiments, after the mesh 820 has been moved to a desirable position with respect to the tissue, a knot (e.g., a tether) can be tied (e.g., tied by a physician) using the suture 819 and/or the loop 817. The needle 830 is shown as a curved needle, but in some embodiments, the needle 830 can be a needle with a different shape such as a straight needle.

In some embodiments, after at least a portion of the hook 815 has been embedded in the tissue 80 via the opening 81, the loop 817 can be decoupled from the hook 815. Accordingly, the hook 815 can function as an anchor in the tissue 80 for the mesh 820.

In some embodiments, after the opening 81 in the tissue 80 has been formed, the needle 830 and the suture 819 can be threaded through the loop 817 (e.g., an opening formed by the loop 817), which is coupled to the hook 815, as shown in FIG. 8B. The mesh 820 can be moved to a desirable position with respect to the tissue 80 using the fixation mechanism 810 (e.g., by tightening the fixation mechanism 810). For example, the needle 830 and suture 819 coupled thereto can be pulled in an upward direction away from the tissue 80 through the loop 817 to cause the mesh 820 (and hook 815) to be moved toward the tissue 80. In some embodiments, a loop 840 formed by the suture 819 threaded through the loop 817 can be coupled to the hook 815. The loop 840 can be used to couple the mesh 820 to the tissue 80.

Finally, excess portions of the suture 819 can be removed after the mesh 820 is moved to a desirable position with respect to the tissue 80 using the fixation mechanism 810. In some embodiments, the mesh 820 (which is coupled to the fixation mechanism 810), the hook 815, the suture 819, the needle 830, and/or a device used to cut the suture 819 can be included in a kit that can be used during a medical procedure.

FIG. 9A illustrates another medical device 900 including a suture 919 coupled to an edge 922 of a mesh 920, according to an embodiment. As shown in FIG. 9A, the medical device 900 includes the mesh 920 and the suture 919 is included in a fixation mechanism 910. The elements included in the medical device 900 may have different relative dimensions than shown in FIGS. 9A. For example, the length of the suture 919 may be shorter or longer than shown in FIGS. 9A and 9B.

As shown in FIG. 9A, the suture 919 is coupled to an edge 922 of the mesh 920. In some embodiments, the suture 919 can be coupled to a top side of the mesh 920 (the flat side of the mesh seen in FIG. 9A), a bottom side of the mesh 920 (the flat side of the mesh that is not visible in FIG. 9A), or any edge of the mesh 920. In this embodiment, fixation mechanisms (not labeled) similar to fixation mechanism 910 can be associated with an edge 924 of the mesh 920, which is on an opposite side of the mesh 920 relative to the edge 922. In some embodiments, the mesh 920 can include more fixation mechanisms or less fixation mechanisms than those shown, and fixation mechanisms can be coupled to any portion (e.g., top side, bottom side, edge 922, edge 924) of the mesh 920. Although not shown in FIG. 9A, the suture 919, and/or the mesh 920 can include one or more barbs. In some embodiments, the suture 919 and the mesh 920 can be made of the same material or of different materials.

As shown in FIG. 9A, a proximal end 918 of the suture 919 can be coupled to a needle 930. The needle 930 can be used to pierce a tissue 90 to form an opening 91 through which the suture 919 can be moved. The mesh 920 can be moved to a desirable position with respect to the tissue 90 by moving the suture 919 through the opening 91, which will cause movement of the mesh 920 attached directly to a distal end 916 of the suture 919. In other words, the mesh 920 can be moved to a desirable position with respect to the tissue 90 using the fixation mechanism 910 (e.g., by tightening the fixation mechanism 910). For example, the needle 930 and suture 919 coupled thereto can be pulled in an upward direction away from the tissue 90 to cause the mesh 920 to be moved toward the tissue 90. In some embodiments, at least a portion of the suture 919 can be embedded in the tissue 90 via the opening 91. Accordingly, the suture 919 can function as an anchor in the tissue 80 for the mesh 820. In some embodiments, after the mesh 920 has been moved to a desirable position with respect to the tissue, a knot (e.g., a tether) can be tied (e.g., tied by a physician) using the suture 919. Finally, excess portions of the suture 919 can be removed after the mesh 920 is moved to a desirable position with respect to the tissue 90 using the fixation mechanism 910. In some embodiments, the mesh 920 (which is coupled to the suture 919), the needle 930, and/or a device used to cut the suture 919 can be included in a kit that can be used during a medical procedure. The needle 930 is shown as a curved needle, but in some embodiments, the needle 930 can be a needle with a different shape such as a straight needle.

Figure 10B:
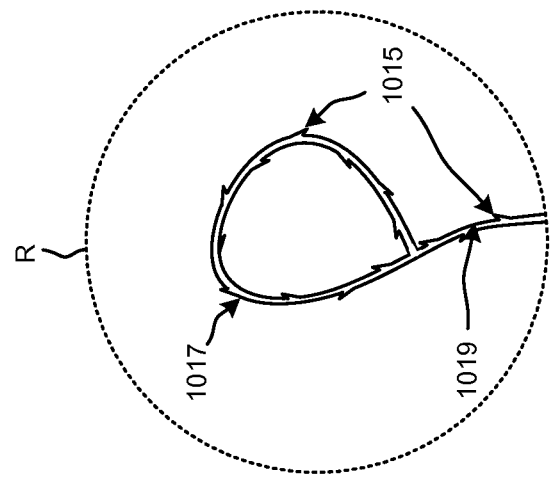
Figure 10A:
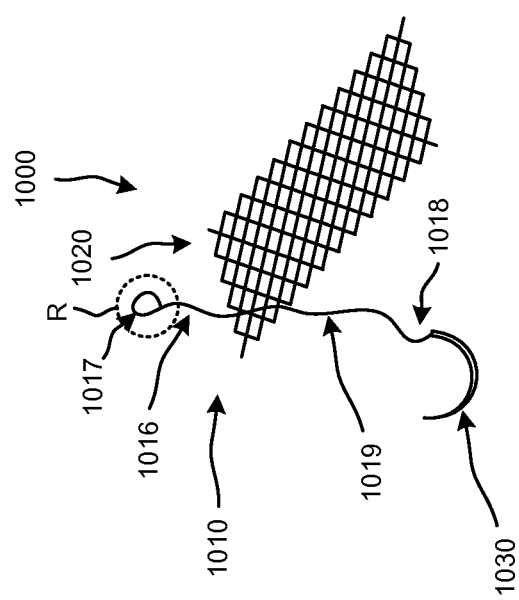

FIGS. 10A through 10E illustrate another medical device 1000, according to an embodiment. As shown in FIG. 10A, the medical device 1000 includes a mesh 1020 and a fixation mechanism 1010. The fixation mechanism 1010 includes a suture-loop member, which includes a loop 1017 and a suture 1019. The loop 1017 is coupled to a proximal end 1016 of the suture 1019. Also, as shown in FIG. 10, the suture 1019 has a distal end 1018 coupled to a needle 1030. In some embodiments, an opening formed by the loop 1017 can have a circular shape, an oval shape, a square shape, and/or so forth. The needle 1030 is shown as a curved needle, but in some embodiments, the needle 1030 can be a needle with a different shape such as a straight needle. In some embodiments, the loop 1017, the suture 1019, and the mesh 1020 can be made of the same material or of different materials. In some embodiments, the loop 1017 may also be prepared as a lasso (or slip knot) where once the suture 1019 is passed through the tissue and passed through the loop 1017, the loop 1017 can be tightened as a physician pulls on the suture 1019. Having a relatively large loop 1017 can facilitate the physician in threading the suture 1019 through the loop 1017 during a procedure.

FIG. 10B is a diagram that illustrates a zoomed-in depiction of portion R of the loop 1017 and the suture 1019 shown in FIG. 10A. As shown in FIG. 10B, the loop 1017 and the suture 1019 include several barbs 1015. In some embodiments, the barbs 1015 can be larger or smaller, relative to the loop 1017 and the suture 1019, than shown in FIG. 10B. Although not shown in FIG. 10B, in some embodiments, different types of barbs with the different densities along the loop 1017 and the suture 1019. Although not shown in in connection with FIGS. 10A through 10E, other portions of the fixation mechanism 1010 and/or of the mesh 1020 of the medical device 1000 can include one or more barbs.

The elements included in the medical device 1000 may have different relative dimensions than shown in FIGS. 10A through 10E. For example, the loop 1017 can be smaller or larger and/or the length of the suture 1019 may be shorter or longer than shown in FIGS. 10A through 10E. An example of a relatively small loop that can be included in FIGS. 10A through 10E is shown and described, for example, in connection with FIGS. 5G and 5H.

FIGS. 10C through 10F that are diagrams that illustrate attachment of the mesh 1020 to a tissue 95. As shown in FIG. 10C, the needle 1030 can be moved through (e.g., completely through) an opening 96 in the tissue 95, which is formed by the needle 1030, so that the suture 1019, which is attached to the needle 1030, can also be moved through the opening 96. As shown in FIG. 10C, the needle 1030 can be threaded through an opening 1021 in the mesh 1020 and through the loop 1017 (e.g., an opening formed by the loop 1017). In this embodiment, the needle 1030 is threaded first through the opening 1021 in the mesh 1020 and subsequently through the loop 1017 (e.g., an opening formed by the loop 1017) so that a loop 1040 is formed through and around at least a portion of the mesh 1020. In some embodiments, the needle 1030 and the suture 1019 can be threaded through multiple openings in the mesh 1020 so that the loop 1040 is formed through and around at least a portion of the mesh 1020.

As shown in FIG. 10D, after the needle 1030 is threaded through the loop 1017, the needle 1030 can be moved in direction away from the tissue 95 so that at least a portion of the mesh 1020 can be moved in an opposite direction toward the tissue 95 (using the opening 96 of the tissue 95 as a pulley). In other words, the mesh 1020 can be moved toward the tissue 95 in a desirable fashion using the fixation mechanism 1010. In some embodiments, the mesh 1020 can be moved toward the tissue 95 by tightening the fixation mechanism 1010 in the manner described above. In some embodiments, the mesh 1020 may not be in contact with (e.g., may be separated from) the tissue 95 after tightening of the fixation mechanism 1010 is performed. In some embodiments, at least a portion of the loop 1017 can be embedded in the tissue 95 via the opening 96. In such embodiments, the mesh 1020 may be in a desirable position with respect to the tissue 95 when the mesh 1020 is not in contact with the tissue 95. In some embodiments, after the mesh 1020 has been moved to a desirable position with respect to the tissue 95, a knot (e.g., a tether) can be tied (e.g., tied by a physician) using the suture 1019 and/or the loop 1017. In some embodiments, any of the mechanisms described above such as an interference mechanism, (e.g., a bead, an umbrella-shaped tether), a barb, and/or so forth can be used to secure the suture 1019 and/or the loop 1017 after the mesh 1020 has been moved to a desirable position with respect to the tissue 95.

Because the loop 1017 and the suture 1019 have barbs 1015, the loop 1017 and the suture 1019 can be prevented (or substantially prevented) from moving out of the opening 96 in the tissue 95. In other words, the barbs 1015 of the suture 1019 can be configured so that when the loop 1017 and/or the suture 1019 has been moved into the tissue 95 in a first direction, the barbs 1015 of the loop 1017 and/or the suture 1019 can prevent (or substantially prevent) the loop 1017 and/or the suture 1019 from moving in a second direction opposite the first direction. In some embodiments, the loop 1017 and/or the suture 1019 may not include barbs 1015. In such embodiments, the loop 1017 and/or the suture 1019 can be slidably moved through the opening 96 of the tissue 95 in the first direction or the second direction.

After the mesh 1020 has been moved to a desirable position with respect to the tissue 95, at least a portion of the suture 1019 (which is coupled to the needle 1030) can be removed (e.g., removed by cutting) as shown in FIG. 10E. In other words, excess portions of the suture 1019 can be removed after the mesh 1020 is moved to a desirable position with respect to the tissue 95. In some embodiments, the mesh 1020, the loop 1017 and suture 1019, the needle 1030, and/or a device used to cut the suture 1019 can be included in a kit that can be used during a medical procedure.

FIGS. 11A and 11B illustrate a mesh 1120 that can be used in conjunction with any of the embodiments described herein. As illustrated in FIG. 11A, a cutting device 1160 can be configured to come in contact with the mesh 1120 so that barbs 1115 are formed in a top surface 1121 of the mesh 1120. In some embodiments, the cutting device 1160 can be moved (e.g., moved along direction N) to come in contact with mesh 1120 at an angle with respect to the mesh 1120 to form the barbs 1115. Specifically, a blade of the cutting device 1160 can be aligned along a plane that forms an angle (e.g., acute angle (e.g., an angle of 45°, an angle of 30°, an angle of 60°)) with a plane along which at least one of the surfaces 1121, 1123 of the mesh 1120 is aligned. In some embodiments, one or more of the barbs 1115 can be configured to provide an interference fit of the mesh 1120 with a tissue. Although not shown in FIGS. 11A and 11B, in some embodiments, a material (e.g., a sheet of a material) having a predefined barbs can be coupled to (e.g., adhesively coupled to) a surface of the mesh 1120.

A zoomed-in depiction of portion S of the mesh 1120 is shown in FIG. 11B. As shown in FIG. 11B, barbs 1115 are on the top surface 1121 the mesh 1120 and are excluded from the bottom surface 1123 of the mesh 1120. An angle X of approximately 45° between the cutting device 1160 and the mesh 1120 is shown. In some embodiments, one or more barbs (such as the barbs 1115) can be formed on the bottom surface 1123 of the mesh 1120.

The top surface 1121, which includes barbs 1115, can be referred to as a barbed side of the mesh 1120. The bottom surface 1123, which does not include barbs (or excludes barbs), can be referred to as a barbless side of the mesh 1120. The top surface 1121 of the mesh 1120 can be a barbless surface until the barbs 1115 are formed on the top surface 1121 using the cutting device 1160.

In some embodiments, barbs such as those shown in FIGS. 11A and 11B can be combined with any of the other fixation mechanisms described herein. For example, barbs such as those shown in FIGS. 11A and 11B can be formed on any of the meshes shown and described in FIGS. 1 through 10E.

Figure 12:
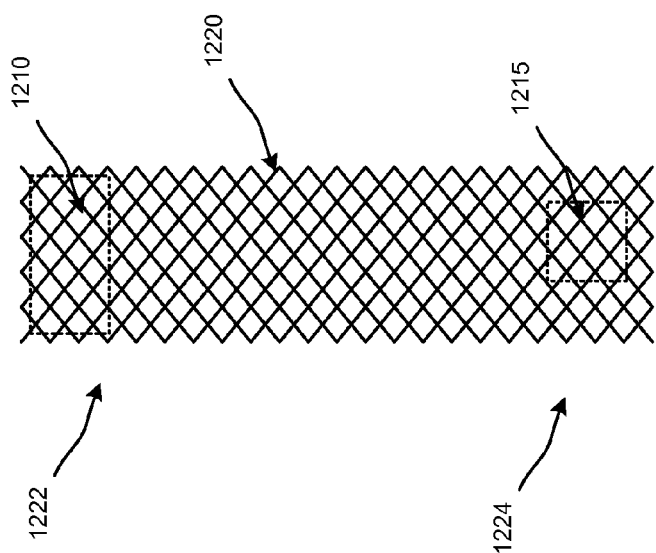
FIG. 12 is a diagram that illustrates a mesh and multiple fixation mechanisms.

FIG. 12 is a diagram that illustrates a mesh 1220 and multiple fixation mechanisms 1210, 1215. In some embodiments, the mesh 1220 can be used in conjunction with any of the embodiments described herein. As shown in FIG. 12, the fixation mechanism 1210 has a surface area that is different than a surface area of the fixation mechanism 1215. In this embodiment, the fixation mechanism 1210 is coupled to an end portion 1222 of the mesh 1220, and the fixation mechanism 1215 is coupled to an end portion 1224 of the mesh 1220.

In some embodiments, one or more of the fixation mechanisms 1210, 1215 can be an adhesive, a set of barbs (e.g., barbs cut into a surface of the mesh 1220), an adhesive that can be applied to the mesh 1220 during a medical procedure, an adhesive protected by a backing material, and/or so forth. Although shown as having rectangular shapes, in some embodiments, one or more of fixation mechanisms 1210, 1215 can have a different shape (e.g., a circular shape, an oval shape, a curved shape).

In some embodiments, the fixation mechanism 1210 and/or the fixation mechanism 1215 can be barbed regions of the mesh 1220. The areas outside of the barbed regions can be referred to as barbless regions of the mesh 1220. When forming a barbed region of a mesh a portion of a side of the mesh can remain barbless while other portions of the side of the mesh can be cut to form barbed regions. Accordingly, a single side of the mesh can have barbed regions and barbless regions. In some embodiments, barbed regions can be isolated by, or separated by, barbless regions. In some embodiments, barbless regions can be isolated by, or separated by, barbed regions.

Although not shown in FIG. 12, in some embodiments, a mesh (such as mesh 1220) can include one or more indicators of one or more areas where one or more fixation mechanisms can be applied. In some embodiments, the indicators can include markings on a surface of the mesh.

Figure 13:
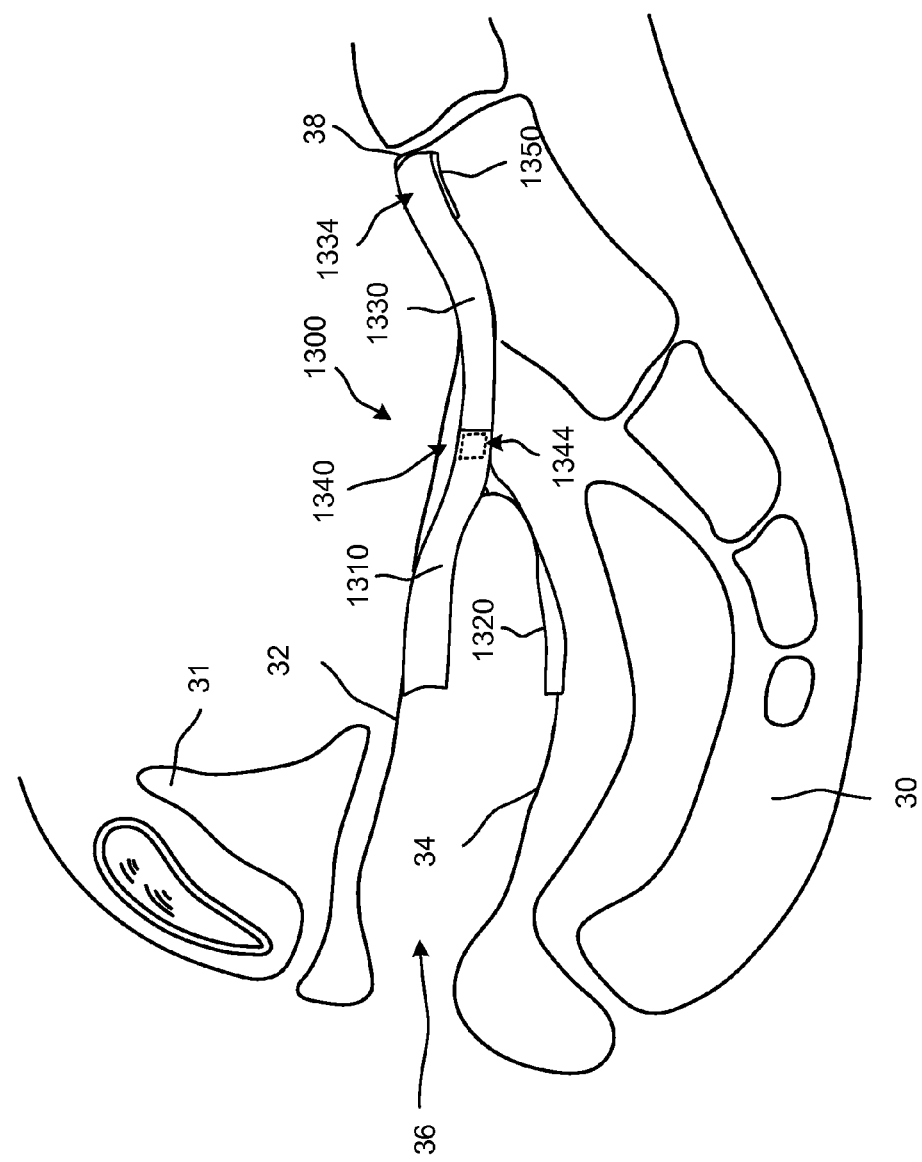
FIG. 13 is a diagram that illustrates placement of a medical device within a body of a patient.

FIG. 13 is a diagram that illustrates placement of a medical device 1300 within a body of a patient. In this embodiment, the medical device 1300 is a Y-shaped mesh that includes a first elongate member 1310, a second elongate member 1320, and third elongate member 1330, which can each be a synthetic mesh and/or a biologic mesh. The medical device 1300 can include any of the features of the medical devices described above (e.g., medical device 100 shown in FIG. 1, medical device 500 shown in FIGS. 5A through 5H, medical device 300 shown in FIGS. 8A and 8B, etc.). The body portions of the patient such as an anterior vaginal wall 32, a posterior vaginal wall 34, a vagina 36, a sacrum 38, buttocks 30, and a bladder 31 are also illustrated in FIG. 13.

As shown in FIG. 13, a first elongate member 1310 is attached to an exterior surface of the anterior vaginal wall 32 and a second elongate member 1320 is attached to an exterior surface of the posterior vaginal wall 34. The first elongate member 1310 can be attached to the exterior surface of the anterior vaginal wall 32 using one or more fixation mechanism such as those described above. Similarly, the second elongate member 1320 can be attached to the exterior surface of the posterior vaginal wall 34 using one or more of the fixation mechanisms described above. A distal end portion 1334 of the third elongate member 1330 is attached to the sacrum 38 of the patient. In some other embodiments, the distal end portion 1334 of the third elongate member 1330 can be attached to another location in close proximity to the sacrum 38 (such as to bodily tissue proximate the sacrum 38). The third elongate member 1330 can be attached to the sacrum 38, or another location in close proximity to the sacrum 38, using one or more of the fixation mechanisms described above. The first elongate member 1310, the second elongate member 1320, and/or the third elongate member 1330 can be made of a synthetic material and/or a biologic material. In this embodiment, the first elongate member 1310, the second elongate member 1320, and the third elongate member 1330 can be coupled using sutures 1344.

In some embodiments, at least a portion of the Y-shaped mesh shown in FIG. 13 may be used as a graft to treat vaginal vault prolapse. The Y-shaped mesh can aid vaginal cuff suspension to the sacrum and may provide long-term support. The procedure can be minimally invasive (such as via a Laparoscopic Sacral Colpopexy) or traditional (such as via an open sacral colpopexy). These Y-shaped meshes may be made of various types of polymeric or biological materials. Various doctors/operators may prefer a particular type of implant to repair the pelvic damage depending on the surgical requirements and a patient's history.

Figure 14:
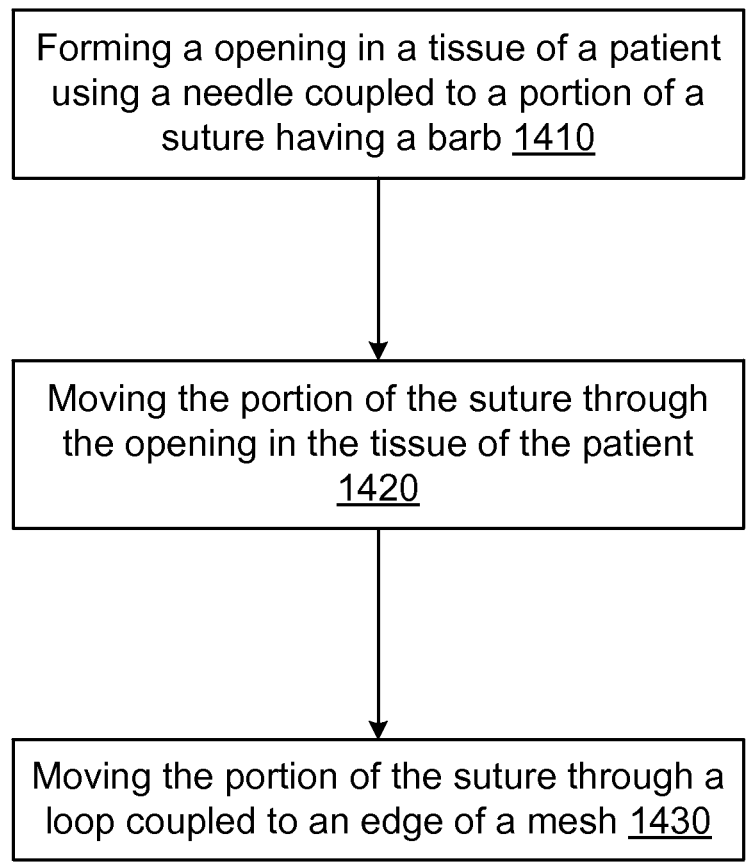
FIG. 14 is a flowchart that illustrates a method for implanting a medical device into a body of the patient.

FIG. 14 is a flowchart that illustrates a method for implanting a medical device into a body of the patient. The medical device can include any of the medical devices described and/or shown above (e.g., medical device 100 shown in FIG. 1, medical device 500 shown in FIGS. 5A through 5H, medical device 300 shown in FIGS. 8A and 8B, etc.).

As shown in FIG. 14, an opening is formed in a tissue of a patient using a needle coupled to a portion of a suture having a barb (block 1410). Prior to forming the opening in the tissue of the patient, the needle can be coupled to the portion of the suture.

The portion of the suture is moved through the opening in the tissue of the patient (block 1420). In some embodiments, the portion of the suture can be moved through the opening in the tissue in response to the needle coupled thereto being pulled. In some embodiments, the suture, and the needle coupled thereto, can be pulled in a direction away from the tissue to cause the mesh to be moved toward the tissue.

The portion of the suture is moved through a loop coupled to an edge of a mesh (block 1430). In some embodiments, the loop can be a first loop coupled to a first edge of the mesh, and a second loop can be coupled to a second edge of the mesh. In some embodiments, the needle can be included in a kit with the mesh, which is coupled to the loop. In some embodiments, after the suture is moved through the loop and the mesh is moved to a desirable position with respect to the tissue, excess portions of the suture can be removed.

Figure 15:
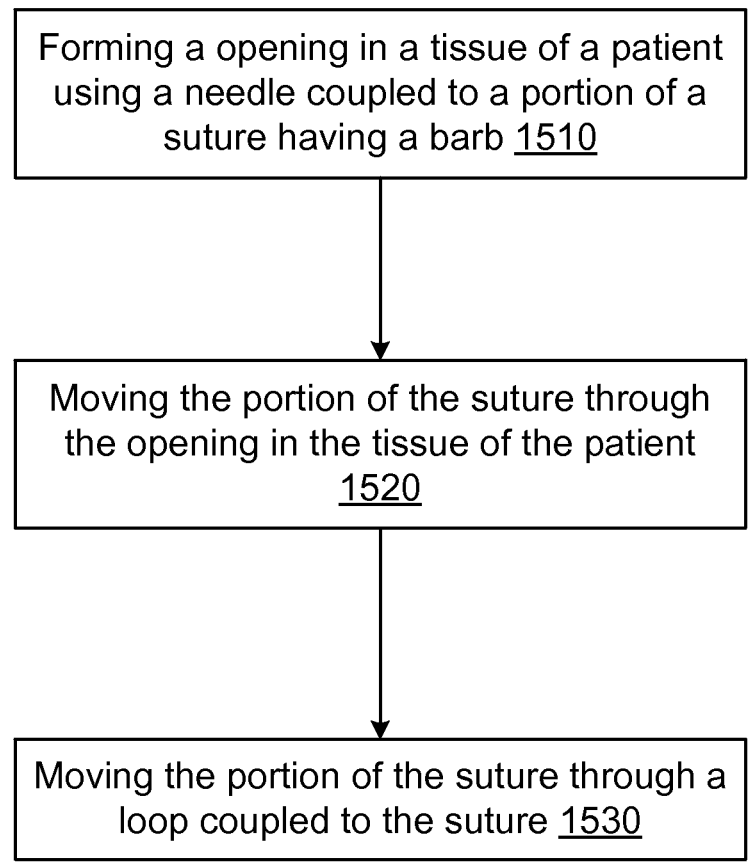
FIG. 15 is another flowchart that illustrates a method for implanting a medical device into a body of the patient.

FIG. 15 is another flowchart that illustrates a method for implanting a medical device into a body of the patient. The medical device can include any of the medical devices described and/or shown above (e.g., medical device 100 shown in FIG. 1, medical device 500 shown in FIGS. 5A through 5H, medical device 300 shown in FIGS. 8A and 8B, etc.).

As shown in FIG. 15, an opening is formed in a tissue of a patient using a needle coupled to a portion of a suture having a barb (block 1510). In some embodiments, prior to forming the opening in the tissue of the patient, the needle can be coupled to the portion of the suture and/or can be moved through an opening in a mesh. In some embodiments, prior to forming the opening in the tissue of the patient, the needle can be coupled to the portion of the suture and/or can be moved through a loop coupled to an edge of a mesh.

The portion of the suture is moved through the opening in the tissue of the patient (block 1520). In some embodiments, the portion of the suture can be moved through the opening in the tissue in response to the needle coupled thereto being pulled. In some embodiments, the suture, and the needle coupled thereto, can be pulled in a direction away from the tissue to cause the mesh to be moved toward the tissue.

The portion of the suture is moved through a loop coupled to the suture (block 1530). In some embodiments, the needle can be included in a kit with the mesh. The loop and the suture can be included in a suture-loop member. In some embodiments, after the suture is moved through the loop and the mesh is moved to a desirable position with respect to the tissue, excess portions of the suture can be removed.

Figure 16:
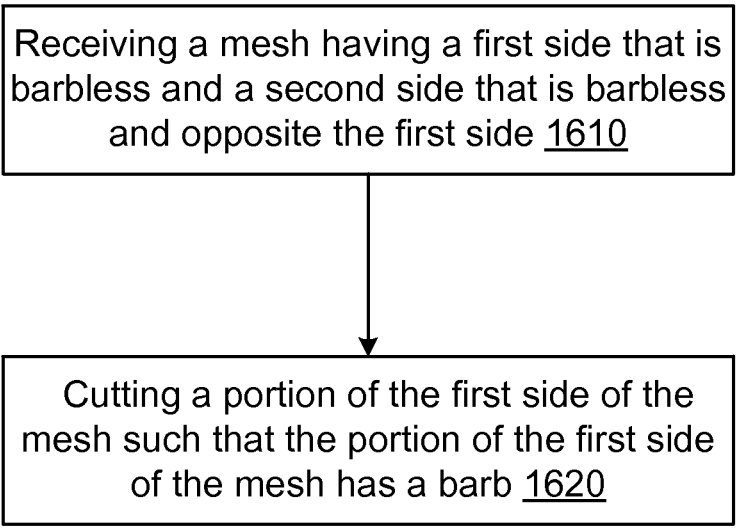
FIG. 16 is a flowchart that illustrates a method for forming a mesh including a barb.

FIG. 16 is a flowchart that illustrates a method for forming a mesh including a barb. As shown in FIG. 16, a mesh having a first side that is barbless and a second side that is barbless and opposite the first side is received (block 1610). A portion of the first side of the mesh can be cut such that the portion of the first side of the mesh has a barb (block 1620). In some embodiments, the one or more barbs can be formed using a cutting device. In some embodiments, one or more barbs can be formed in a first region (or first portion) on the first side the mesh while a second region (or second portion) on the first side of the mesh remains barbless. In some embodiments, a barbed region can be isolated from other barbed regions by barbless regions. In some embodiments, a barbless region can be isolated from other barbless regions by barbed regions.

In one general aspect, an apparatus can have a implant having an edge, a loop coupled to the edge of the implant, and a suture coupled to at least one of the loop or the edge of the implant, the suture having a barb. The loop can have an inner diameter smaller than a combined width of the suture and at least a portion of an outer portion of the barb.

In some embodiments, the suture has a first end portion coupled to at least one of the loop or the edge of the implant, and the apparatus can include a needle coupled to a second end portion of the suture. In some embodiments, the loop extends from the edge and is aligned along a plane that is aligned along a flat portion of the implant. In some embodiments, the loop is formed by a suture having a first end fixedly coupled to the edge and a second end fixedly coupled to the edge.

In some embodiments, the implant is a mesh.

In some embodiments, the loop and the barb are configured so that an outer portion of the barb can move through an opening of the loop in a first direction when the outer portion of the barb is engaged with the loop and configured so that an inner portion of the barb is prevented from moving through the opening of the loop in a second direction opposite the first direction when the inner portion of the barb is engaged with the loop. In some embodiments, the at least one of the implant or the loop has a barb.

In some embodiments, the edge is a first edge of the implant, the loop is a first loop. The apparatus can include a second loop coupled to a second edge of the implant different from the first edge of the implant. In some embodiments, the edge is a first edge of the implant, and the loop is a first loop. The apparatus can include a second loop coupled to the first edge of the implant. In some embodiments, the suture and the loop are made of the same material as the implant. In some embodiments, the suture is coupled to a curved needle.

In another general aspect, a method can include forming a opening in a tissue of a patient using a needle coupled to a portion of a suture having a barb during a medical procedure, moving the portion of the suture through the opening in the tissue of the patient, and moving the portion of the suture through a loop coupled to an edge of a implant. The method can also include pulling the portion of the suture, after the moving of the portion of the suture through the loop, to cause the implant to move toward the tissue. The method can also include cutting the suture after the moving the portion of the suture through the loop.

In some embodiments, the medical procedure is a sacrocolpopexy procedure. In some embodiments, the suture is made of the same material as the implant. In some embodiments, the suture is coupled to the edge of the implant. In some embodiments, the suture is coupled to the loop.

In another general aspect, a method can include receiving a implant having a first side that is barbless and a second side that is barbless and opposite the first side, and can include cutting a portion of the first side of the implant such that the portion of the first side of the implant has a barb.

In some embodiments, the cutting includes cutting at an acute angle with respect to a plane aligned along a flat surface of the implant. In some embodiments, the portion is a first portion, and the method can include cutting a second portion of the first side of the implant such that the second portion of the first side of the implant has a barb and is separated from the first portion of the implant by a barbless region.

Detailed embodiments are disclosed herein; however, it is to be understood that the disclosed embodiments are merely exemplary embodiments, which may be implemented in various forms. Therefore, specific structural and functional details disclosed herein are to be interpreted as non-limiting, and as a basis for the claims and as a representative. In other words, while the disclosure includes preferred embodiments shown and described in detail, various modifications and improvements thereon will become readily apparent to those skilled in the art. Any portion of the apparatus and/or methods described herein may be combined in any combination, except mutually exclusive combinations. The embodiments described herein can include various combinations and/or sub-combinations of the functions, components, and/or features of the different embodiments described. Further, the terms and phrases used herein are not intended to be limiting, but to provide an understandable description of the invention. Accordingly, the spirit and scope of the present embodiments, are not to be limited by the foregoing examples, but it is to be understood in the broadest sense permitted.

What is claimed is:

1. An apparatus, comprising:
   an implant including a mesh, the mesh having a first edge and a second edge, the second edge being opposite to the first edge;
   a loop fixedly coupled to the first edge of the mesh, the loop being fixedly coupled to a first location of the first edge of the mesh, the loop having an inner diameter defining a loop opening;
   a needle; and
   a suture having a first end portion and a second end portion, the first end portion of the suture being fixedly coupled to a second location of the first edge of the mesh, the second end portion of the suture being coupled to the needle, the suture having a portion defining a barb, the portion of the suture defining the barb being disposed between the first end portion and the second end portion,
   wherein the needle and the portion of the suture defining the barb are configured to be inserted through bodily tissue.

2. The apparatus of claim 1, wherein the portion of the suture defining the barb has a width that is greater than the inner diameter of the loop opening.

3. The apparatus of claim 2, wherein the barb is flexible such that the portion of the suture defining the barb is configured to be inserted through the loop opening in a first direction, the portion of the suture defining the barb configured to engage with the loop such that the portion of the suture defining the barb is substantially prevented from moving in a second direction opposite to the first direction.

4. The apparatus of claim 1, wherein the loop is aligned along a plane that is aligned along a plane of the mesh.

5. The apparatus of claim 1, wherein the suture is a first suture, and the loop is formed by a second suture having a first end fixedly coupled to the first edge of the mesh and a second end fixedly coupled to the first edge of the mesh.

6. The apparatus of claim 1, wherein at least one of the implant or the loop has a barb.

7. The apparatus of claim 1, wherein
   the apparatus further comprises:
   a second loop coupled to the second edge of the mesh.

8. The apparatus of claim 7, wherein the apparatus further comprises:
   a third loop coupled to the first edge of the mesh at a third location along the first edge of the mesh.

9. The apparatus of claim 1, wherein the suture and the loop are made of the same material as at least a portion of the implant.

10. The apparatus of claim 1, wherein the needle includes a curved portion.

11. A method, comprising:
    forming an opening in a tissue of a patient using a needle coupled to a portion of a suture having a barb during a medical procedure;
    moving the portion of the suture through the opening in the tissue of the patient; and
    moving the portion of the suture through a loop opening of a loop in a first direction, the loop being coupled to an edge of a mesh of an implant, the loop having an inner diameter defining the loop opening; and engaging the barb with the loop as the suture is moved in a second direction opposite to the first direction, the suture being substantially prevented from moving through the loop opening in the second direction.

12. The method of claim 11, further comprising:
pulling the portion of the suture, after the moving of the portion of the suture through the loop, to cause the implant to move toward the tissue.

13. The method of claim 11, further comprising:
cutting the suture after the moving the portion of the suture through the loop.

14. The method of claim 11, wherein the medical procedure is a sacrocolpopexy procedure.

15. The method of claim 11, wherein the suture is made of the same material as at least a portion of the implant.

16. The method of claim 11, wherein the suture is coupled to the edge of the mesh.

17. The method of claim 11, wherein the suture is coupled to the loop.

* * * * *